United States Patent [19]

Green et al.

[11] Patent Number: 4,728,020
[45] Date of Patent: Mar. 1, 1988

[54] ARTICULATED SURGICAL FASTENER APPLYING APPARATUS

[75] Inventors: David T. Green, Norwalk; Ernie Aranyi, Shelton, both of Conn.

[73] Assignee: United States Surgical Corporation, Norwalk, Conn.

[21] Appl. No.: 771,845

[22] Filed: Aug. 30, 1985

[51] Int. Cl.⁴ .............................................. A61B 17/00
[52] U.S. Cl. ...................................... 227/19; 227/110; 227/DIG. 1
[58] Field of Search .............. 128/334 R, 305; 227/19, 227/110, 111, DIG. 1; D24/26, 27; 72/409, 410

[56] References Cited

U.S. PATENT DOCUMENTS

| | | | |
|---|---|---|---|
| D. 274,096 | 5/1984 | Shutt | D24/27 |
| 3,949,924 | 4/1976 | Green | 227/132 |
| 4,185,762 | 1/1980 | Froelich | 227/138 |
| 4,196,836 | 4/1980 | Becht | 227/110 |
| 4,204,623 | 5/1980 | Green | 227/19 |
| 4,440,170 | 4/1984 | Golden et al. | 128/325 |
| 4,471,781 | 9/1984 | DiGiovanni et al. | 128/334 R |
| 4,473,077 | 9/1984 | Noiles et al. | 128/305 |
| 4,485,817 | 12/1984 | Swiggett | 128/334 R |
| 4,488,523 | 12/1984 | Shichman | 128/334 R |
| 4,573,622 | 3/1986 | Green et al. | 227/19 |
| 4,576,167 | 3/1986 | Noiles | 227/DIG. 1 |
| 4,580,712 | 4/1986 | Green | 227/19 |
| 4,606,343 | 8/1986 | Conta et al. | 227/DIG. 1 |

FOREIGN PATENT DOCUMENTS 0140552 8/1985 European Pat. Off. .
869388 3/1953 Fed. Rep. of Germany .
869527 3/1953 Fed. Rep. of Germany .

OTHER PUBLICATIONS

"Instructions for Use; PROXIMATE ™ Flexible Linear Stapler", Ethicon, Inc., Somerville, N.J., copyright 1983.

*Primary Examiner*—Paul A. Bell
*Attorney, Agent, or Firm*—Kenyon & Kenyon

[57] ABSTRACT

Surgical fastener applying apparatus having an articulated shaft assembly intermediate a proximal actuator assembly and a distal fastener applying assembly. The rotational axis of the articulation is transverse to the proximal-distal axis of the shaft assembly. The apparatus is fully operational at any rotational position of the articulation. A detent mechanism may be included to releasably hold the articulation in any of its rotational positions. A locking mechanism may also be provided for locking the articulation in any of its rotational positions. The shaft assembly may also include a second articulation whose rotational axis is the proximal-distal axis. The apparatus is fully operational at any rotational position of the second articulation, and detent and locking mechanisms may also be associated with the second articulation.

23 Claims, 21 Drawing Figures

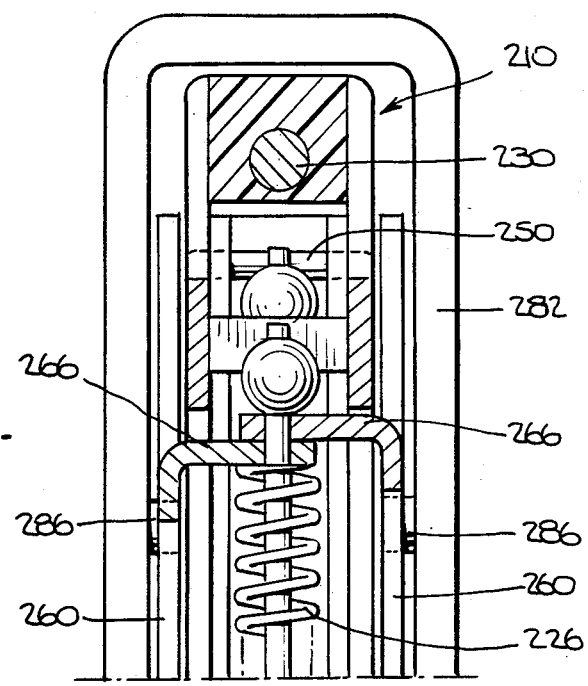
Fig.14.
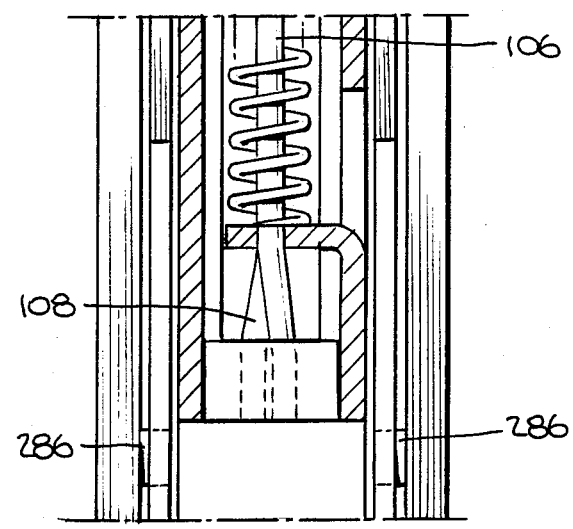
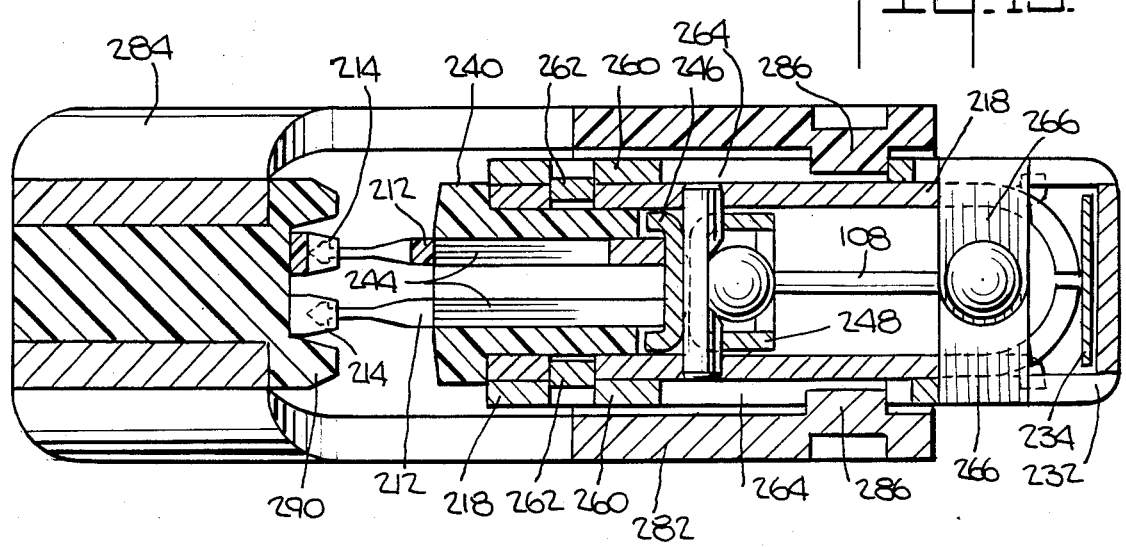
Fig.15.

ARTICULATED SURGICAL FASTENER APPLYING APPARATUS

BACKGROUND OF THE INVENTION

This invention relates to surgical fastener applying apparatus, and more particuarly to surgical fastener applying apparatus of the type that applies surgical fasteners to body tissue clamped between relatively movable fastener holding and anvil parts of the apparatus.

Several types of surgical fastener applying instruments are known for applying surgical fasteners to body tissue clamped between relatively movable fastener holding and anvil parts of the apparatus. See, for example, Hirsch et al. U.S. Pat. No. 3,275,211. The surgical fasteners may be either metal staples as shown in the Hirsch et al. patent, or they may be non-metallic resinous materials as shown, for example, in Green U.S. Pat. No. 4,402,445. In the case of metal staples, the staple legs are typically driven through the tissue and clinched by the anvil to secure the staples in the tissue. In the case of non-metallic fasteners, each fastener may initially consist of two separate parts: a fastener part disposed in the fastener holding part of the apparatus, and a retainer part disposed in the anvil part of the apparatus. The leg or legs of the fastener parts are driven through the tissue and interlock with the retainer parts to secure the fasteners in the tissue. Although most metal surgical staples are biologically inert and therefore remain permanently in the body, biologically absorbable metal surgical staples are known. Surgical fasteners of non-metallic resinous materials can also be made either biologically absorbable or non-absorbable.

The type or form of the fasteners employed forms no part of the present invention. As used herein, the term "surgical fastener" is generic to all of the above-mentioned fastener types. Similarly, the terms "fastener holding part" and "anvil part" are also used generically herein.

In most of the known instruments for applying surgical fasteners to tissue clamped between the fastener holding and anvil parts of the instrument, the distal fastener applying assembly (which includes the fastener holding and anvil parts) of the instrument is rigidly connected to the proximal actuator portion of the instrument. This is true, for example, of the instruments shown in the abovementioned Hirsch et al. and Green patents.

Recently, however, there has been increasing interest in instruments in which the connection between the fastener applying assembly and the actuator assembly is not completely rigid. For example, Noiles et al. U.S. Pat. No. 4,473,077 shows a surgical stapler in which the shaft assembly connected between the fastener applying and actuator assemblies is transversely flexible in one plane (i.e., the plane of the paper in Noiles et al. FIG. 5). This may be a desirable feature in an instrument of the type shown by Noiles et al. which is intended for insertion into a tubular body organ. In such applications, the flexible shaft of the instrument conforms to the curvature of the surrounding body organ. However, in instruments which are not usually supported by surrounding body structures (e.g., instruments of the type shown in the above-mentioned Hirsch et al. and Green patents), excessive flexibility in the instrument between the fastener applying and actuator assemblies may mean that the location of the fastener applying assembly cannot be controlled from the actuator assembly and that each of these assemblies must be separately supported during placement of the instrument relative to the tissue to be fastened. This may mean that two people are required to handle the instrument during placement and removal.

In view of the foregoing, it is an object of this invention to provide surgical fastener applying apparatus of the type described above in which the fastener applying assembly is not rigidly connected to the actuator assembly, but in which the location of the fastener appying assembly can be substantially controlled from the actuator assemby.

It is another object of this invention to provide surgical fastener applying apparatus of the type described above in which the fastener applying assembly is not rigidly connected to the actuator assembly, but in which the fastener applying assembly can be completely controlled from the actuator assembly with the fastener applying assembly in any position relative to the actuator assemby.

SUMMARY OF THE INVENTION

These and other objects of the invention are accomplished in accordance with the principles of the invention by providing surgical fastener applying apparatus in which the fastener applying assembly is connected to the actuator assembly by a longitudinal shaft assembly including an articulation for allowing rotation of the fastener applying assembly relative to the actuator assembly about an axis which is transverse to the longitudinal axis of the shaft assembly. The shaft assembly is operative in any rotational position of the articulation to transmit from the actuator assembly to the fastener applying assembly the forces and motions ("work") necessary to operate the fastener applying assembly. The shaft assembly is also preferably rigid about all other axes parallel to the axis of rotation of the above-described articulation.

In the preferred embodiment, multi-position detent means are associated with the articulation to releasably retain the articulation in any of a plurality of rotational positions. Locking means may also be provided to lock the articulation in any of a plurality of rotational positions. Stop means may also be associated with the articulation to confine the articulation to a predetermined rotational range. Both the tissue clamping operation and the fastener applying operation are preferably completely controlled from the actuator assembly, and the necessary work is preferably transmitted from the actuator assembly to the fastener applying assembly by shaft assembly members which are proximally movable tension force transmitting members. These members are preferably transversely flexible adjacent to the articulation, and pass through the articulation along axes which are coincident with the axis of rotation of the articulation. The fastener applying part of the apparatus is preferably mounted at a fixed distance from the main body of the actuator assembly, and the anvil part is mounted so that it moves toward the fastener holding part in response to appropriate operation of the actuator assembly.

If desired, the shaft assembly may also include a second articulation for allowing rotation of the fastener applying assembly relative to the actuator assembly about the longitudinal axis of the shaft assembly. As in the case of the first articulation, the shaft assembly is operative in any rotational position of the second articulation to transmit from the actuator assembly to the fastener applying assembly the work necessary to operate the fastener applying assembly. Any or all of detent means, locking means, and stop means may be associated with the second articulation in a manner similar to the association of such elements with the first articulation.

Further features of the invention, its nature and various advantages will be more apparent from the accompanying drawings and the following detailed description of the invention.

BRIEF DESCRIPTION OF THE DRAWINGS

FIGS. 10 and 11 show the same operating cycle stages as are shown in FIGS. 3 and 4, respectively.

FIG. 14 is a sectional view taken along the line 14—14 in FIG. 10.

FIG. 15 is a sectional view taken along the line 15—15 in FIG. 12.

DETAILED DESCRIPTION OF THE INVENTION

I. Overall Construction and Operation

Figure 1:
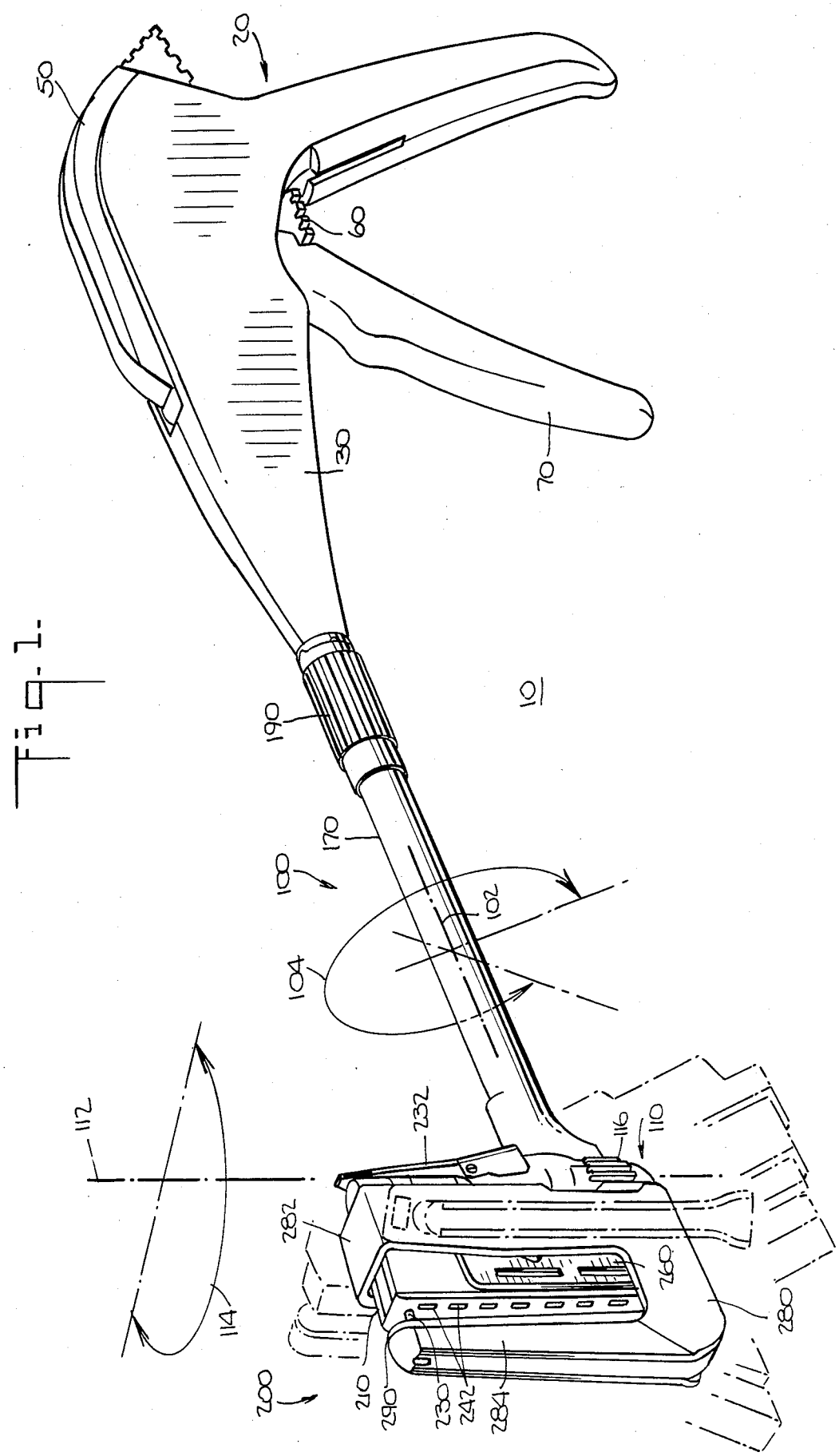
FIG. 1 is a perspective view of an illustrative embodiment of the surgical fastener applying apparatus of this invention.

As shown in FIG. 1, an illustrative embodiment of the surgical fastener applying apparatus or instrument 10 of this invention includes proximal actuator assembly 20, distal fastener applying assembly 200, and intermediate shaft assembly 100.

Fastener applying assembly 200 includes proximal fastener holding part 210 which is mounted on the distal end of shaft assembly 100 for rotation by hand about axis 112, the rotational axis of first articulation 110. It should be noted that axis 112 is transverse to the longitudinal axis 102 of shaft assembly 100. In particular, axis 112 is perpendicular to axis 102, although that is not necessarily the case. It should also be noted that axis 112 is parallel to the longitudinal axis of fastener holding part 210, although again that is not necessarily the case. Articulation 110 allows fastener applying assembly 200 to be moved to any rotational position about axis 112 within the limits indicated by the ends of double-headed arrow 114 in FIG. 1. In the depicted embodiment, fastener holding assembly 200 can be rotated approximately 90° to either side of axis 102 (total rotation approximately 180°).

Shaft assembly 100 also includes a second articulation 140, the components of which are best seen in FIGS. 16-20 and which is described in greater detail below. In general, articulation 140 allows the distal portion (including articulation 110) of shaft assembly 100 to be rotated by hand relative to the proximal portion of the shaft assembly about longitudinal axis 102. Thus, articulation 140 allows fastener applying assembly 200 to be moved to any rotational position about axis 102 within the limits indicated by the ends of double headed arrow 104 in FIGS. 1 and 20. Preferably, actuator assembly 200 can be rotated about axis 102 at least about 90° in either direction from the position shown in FIG. 1 (total rotation at least about 180°), more preferably approximately 150° in either direction from the position shown in FIG. 1 (total rotation approximately 300°).

A U-shaped frame 280 is movably mounted on fastener holding part 210. In particular, the proximal leg 282 of frame 280 is adjacent fastener holding part 210, while the distal leg 284 of frame 280 is distally spaced from fastener holding part 210. Anvil part 290 is mounted on distal leg 284.

Figure 2:
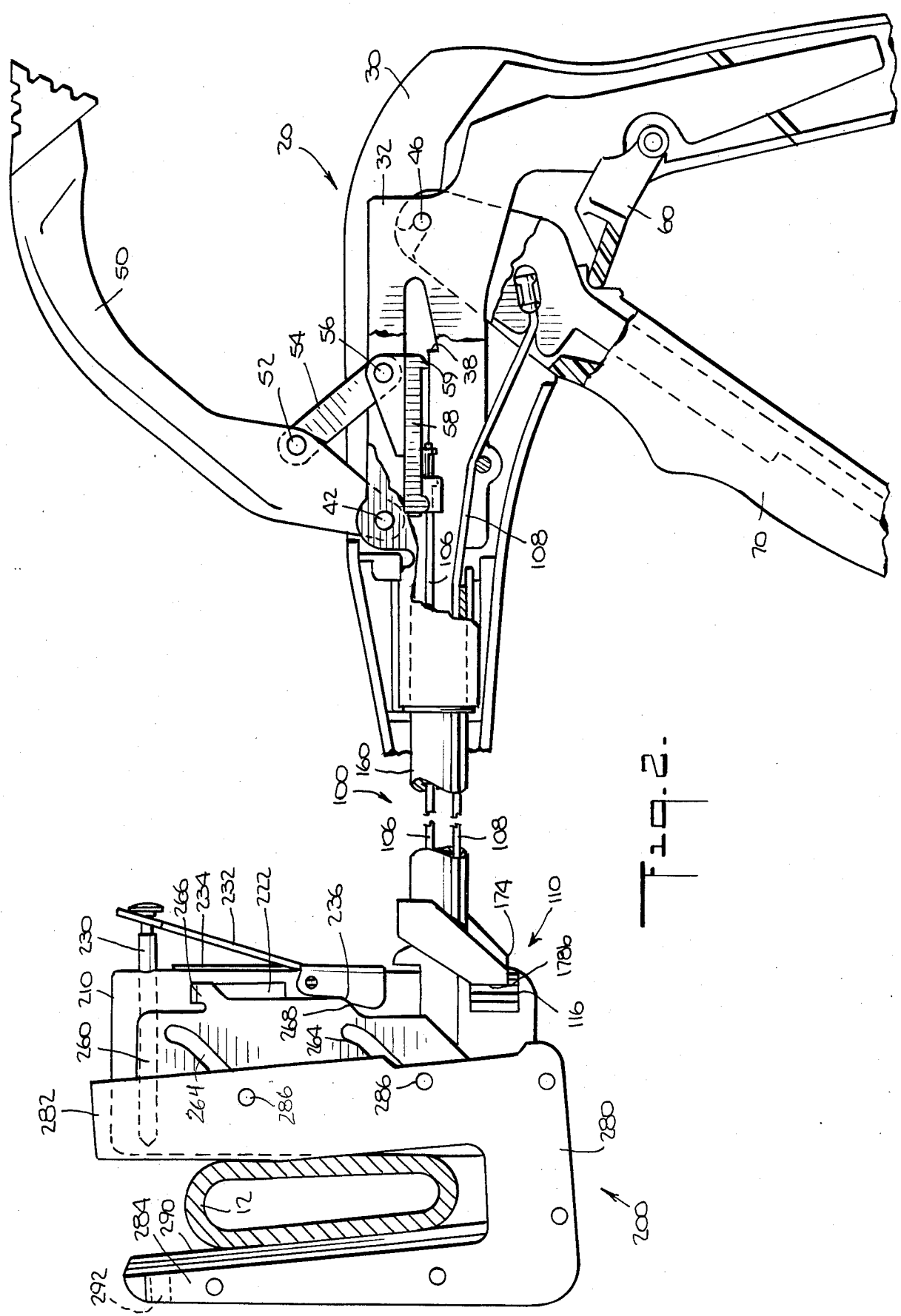
FIG. 2 is a partly sectional elevational view of the apparatus of FIG. 1 showing an initial stage in the operating cycle of that apparatus.

In use, after fastener applying assembly 200 has been properly oriented by manual operation of articulations 110 and 140, tissue 12 to be fastened is located between fastener holding part 210 and anvil part 290 with those parts spaced apart as shown in FIG. 2. Clamp actuator 50 is then pivoted down by hand toward the main body 30 of actuator assembly 20 as is shown progressively in FIGS. 3 and 4. This causes frame 280 to translate in the proximal direction, thereby clamping tissue 12 between fastener holding part 210 and anvil part 290. The tissue can now be fastened. This is accomplished by manualy pivoting safety latch 60 down to the dotted line position shown in FIG. 4 and manually pivoting fastener actuator 70 back toward the dotted line position also shown in FIG. 4. This causes fastener holding part 210 to drive a plurality of surgical fastener parts 212 (FIGS. 9-13 and 15) from fastener holding part 210, partly through tissue 12, and into interlocking engagement with retainer parts 214 which are removably mounted in anvil part 290. The tissue fastening procedure is now complete and instrument 10 is removed from the tissue by manually pivoting clamp actuator 50 away from main body 30 to cause anvil part 290 to move distally away from fastener holding part 210, thereby releasing the clamping pressure on the tissue. After use as described above, instrument 10 is discarded.

Instrument 10 is fully operational in any rotational positions of articulations 110 and 140. Articulations 110 and 140 allow the surgeon to select any of a wide range of positons of fastener holding assembly 200 relative to actuator assembly 20, thereby greatly facilitating placement and use of instrument 10. Except for articulations 110 and 140 (and the moving parts associated with each of assemblies 20, 100, and 200), instrument 10 is a rigid structure. For example, there is no other axis parallel to axis 112 about which instrument 10 is flexible to any degree. This fact, combined with the detent and locking means associated with each articulation as described in detail below, allows the surgeon to first select the desired relative rotational positions of assemblies 20 and 200, and to thereafter fully control placement and operation of the instrument from the proximal end of the instrument.

Although in the depicted embodiment the tissue is fastened by means of two-part interlocking fasteners which are typicaly made of a non-metalic resinous material, those skilled in the art will appreciate that metal surgical staples could also be used. Similarly, although depicted instrument 10 is designed to be discarded after a single use (thereby allowing the hospital to avoid all difficulty and expense associated with cleaning, sterilzing, and reloading the instrument for reuse), those skilled in the art will also appreciate that the apparatus could be made permanent and reusable if desired.

11. Detailed Construction and Operation of Actuator Assembly 20

Considering now the construction and operation of actuator assembly 20 in relation to FIGS. 2–5, main body 30 is made up of an interior frame structure 32 surrounded by two mirror-image shell members 34 and 36. Clamp actuator 50 is pivotally connected to main body 30 by means of pivot pin 42. Clamp actuator 50 is also pivotally connected by pivot pin 52 to one end of toggle link 54. The other end of toggle link 54 is pivotally connected by pivot pin 56 to clamp actuator cable anchor 58. Anchor 58 is mounted in main body 30 for reciprocal motion parallel to axis 102. The proximal end of clamp actuator cable 106 is fixedly attached to anchor 58.

Figure 3:
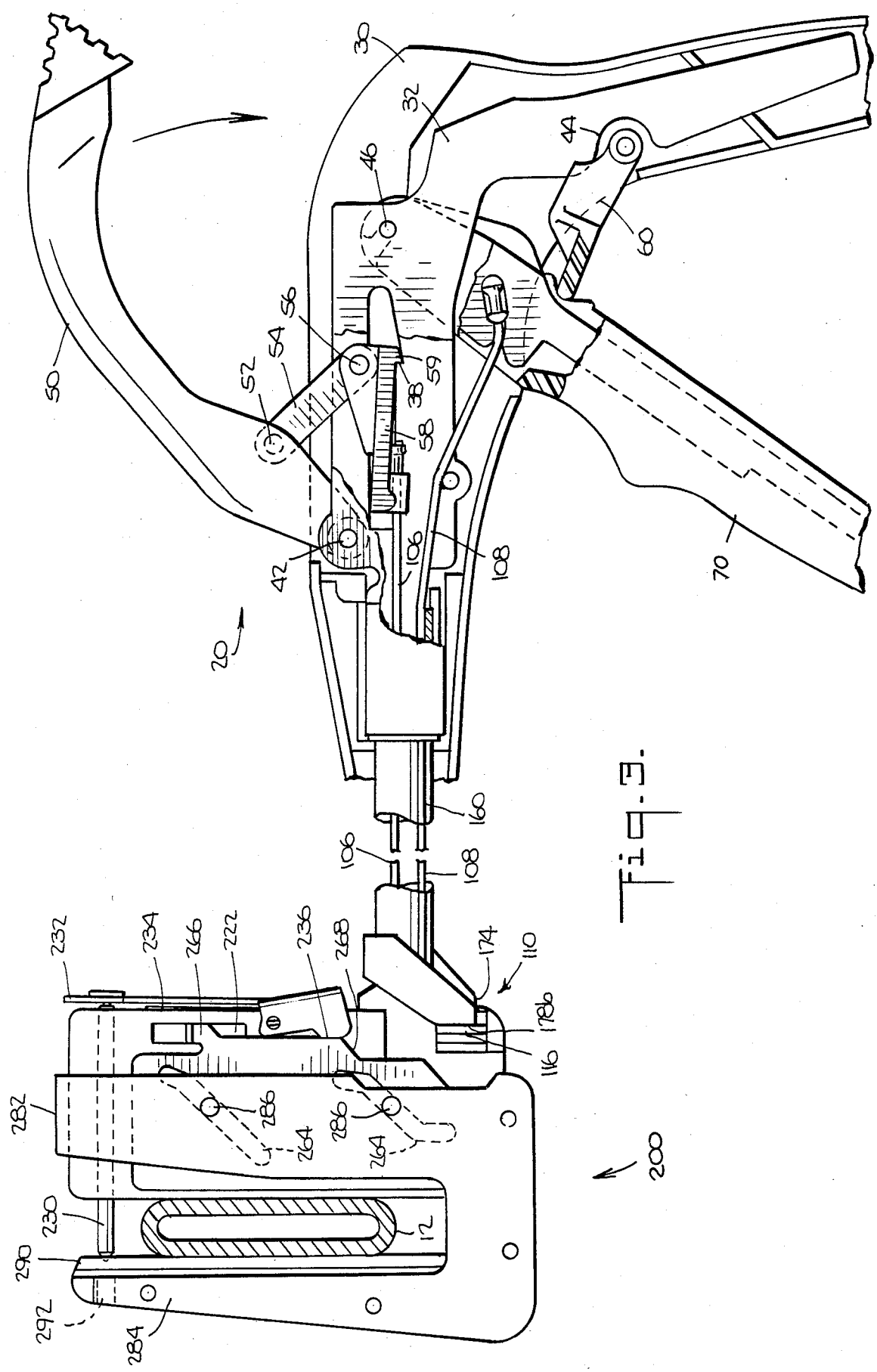
FIGS. 3 and 4 are views similar to FIG. 2 showing successive stages in the operating cycle of the apparatus of FIG. 1.
Figure 4:
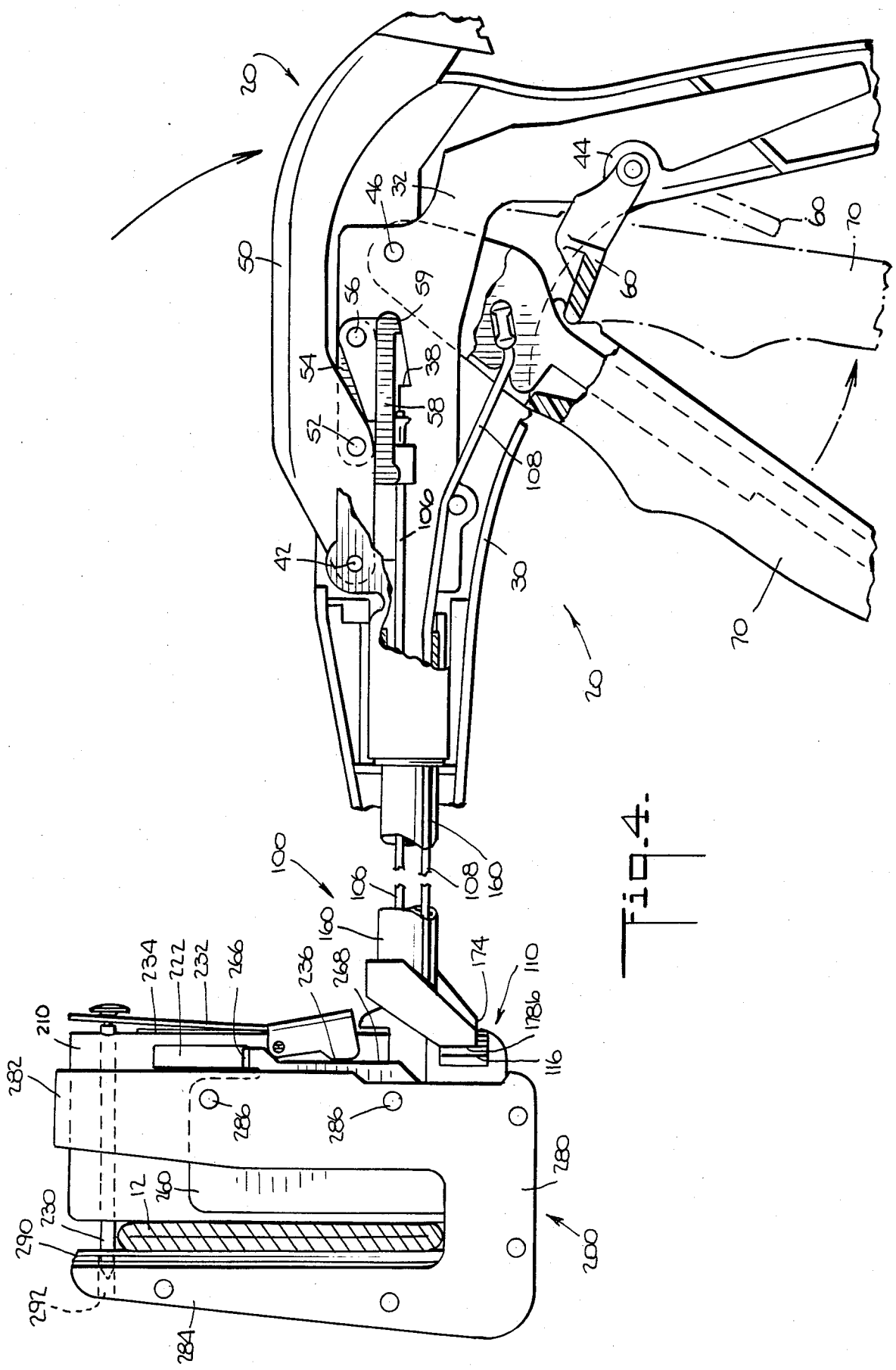
Figure 5:
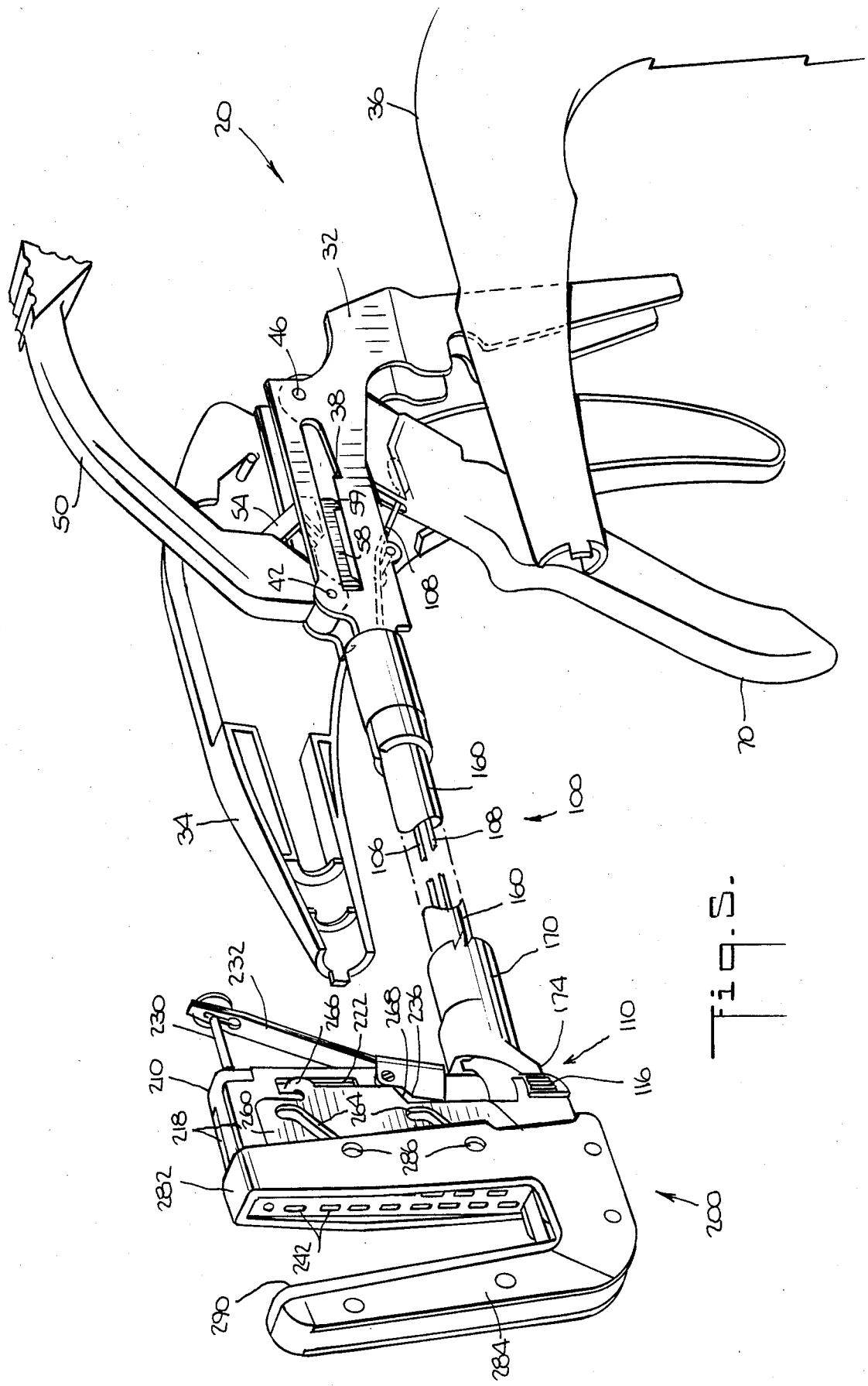
FIG. 5 is a partly exploded perspective view of the apparatus of FIG. 1 in the condition shown in FIG. 2.
Figure 6:
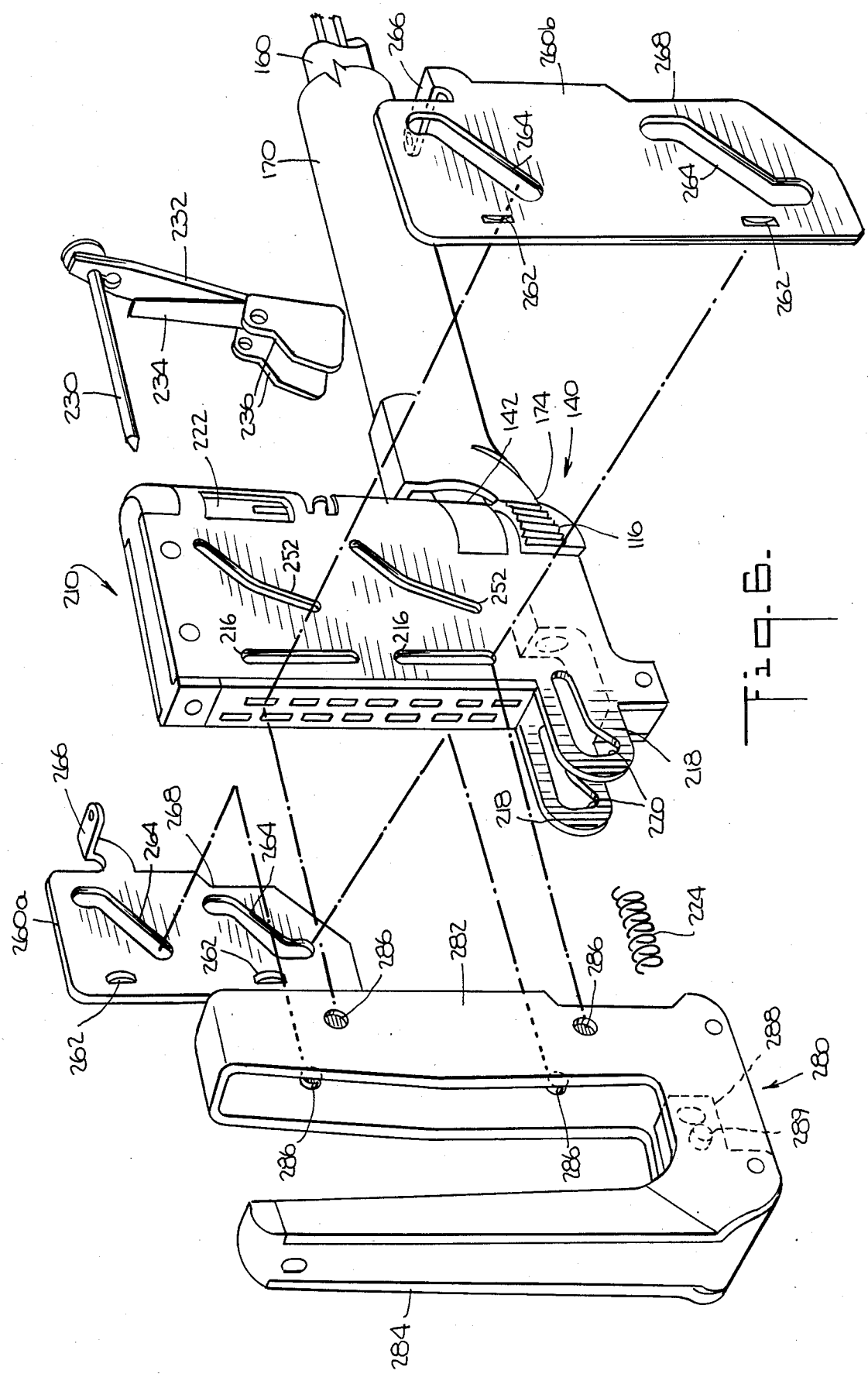
FIG. 6 is a partly exploded perspective view of the distal portion of the apparatus of FIG. 1.
Figure 7:
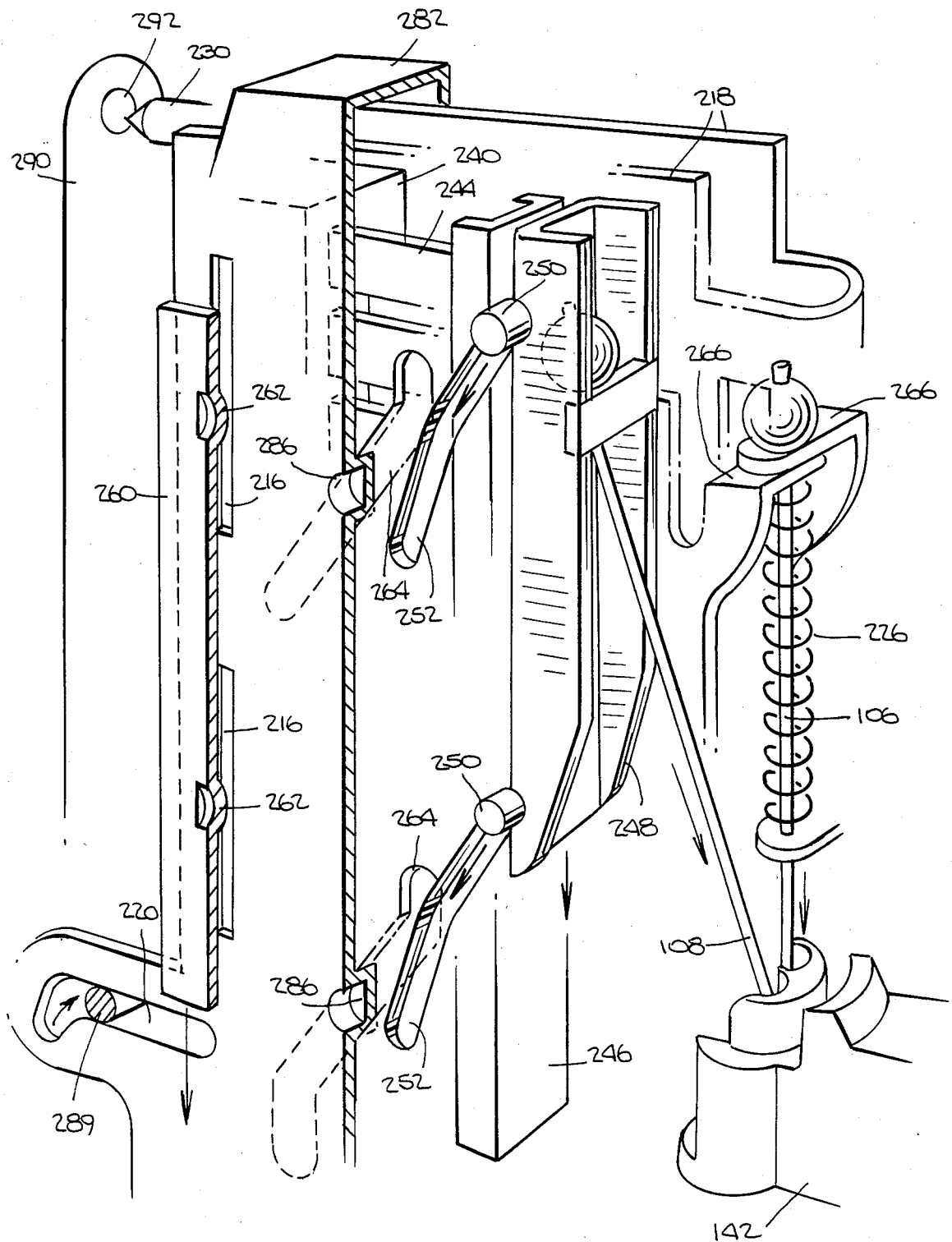
FIG. 7 is a fragmentary perspective view of the distal portion of the apparatus of FIG. 1.
Figure 8:
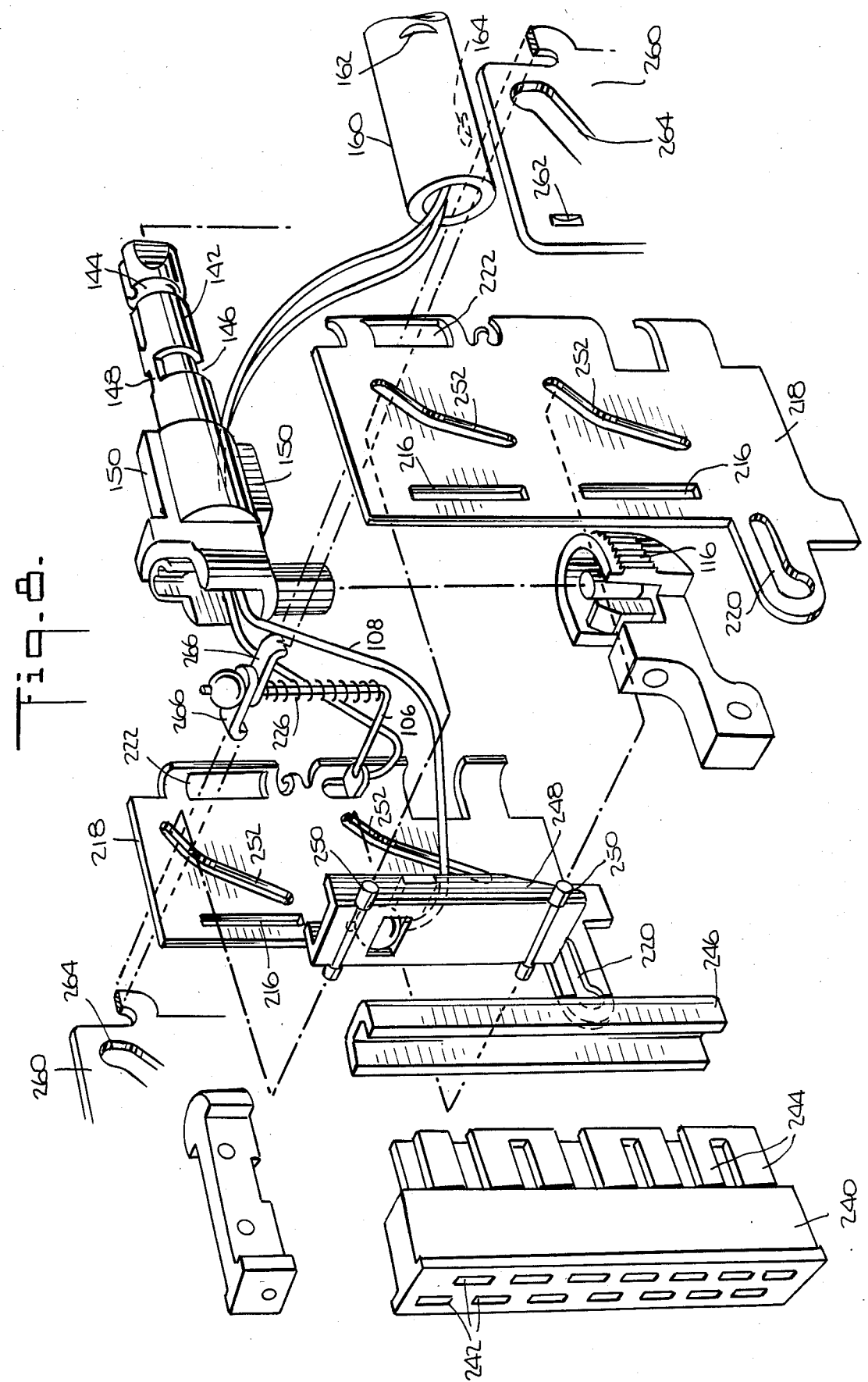
FIG. 8 is a further exploded perspective view of the distal portion of the apparatus of FIG. 1.

When clamp actuator 50 is pivoted down toward main body 30 as is shown progressively in FIGS. 2-4, toggle ink 54 causes anchor 58 to move in the proximal direction. Cable 106 is pulled in the proximal direction by anchor 58. Anchor 58 is releasably retained in the intermediate rest position shown in FIG. 3 by engagement of anchor tooth 59 with frame step 38. This holds actuator assembly 200 in the position shown in FIG. 3 even though the manual pivoting force has been removed from clamp actuator 50. The surgeon is thereby afforded an opportunity to inspect and, if necessary, adjust the placement of the instrument relative to tissue 12 while the tissue is substantially enclosed within fastener applying assembly 200 but before full clamping pressure has been applied to the tissue. If desired, the instrument can be reopened by lifting up on clamp actuator 50, thereby lifting anchor tooth 59 over step 38. Anchor 58 is also releasably retained in the proximal position shown in FIG. 4 by virtue of the fact that in that position, pivot pin 52 is slightly over center (i.e., slightly below a line connecting pivot pins 42 and 56 as viewed in FIG. 4). Once again, the instrument can be reopened from this position by lifting up on clamp actuator 50.

Safety latch 60 is pivotally oonnected to main body 30 by pivot pin 44, and fastener actuator 70 is pivotally connected to main body 30 by pivot pin 46. The proximal end of fastener actuator cable 108 is fixedly attached to fastener actuator 70. Cable 108 is pulled in the proximal direction when fastener actuator 70 is pivoted as shown in FIG. 4.

III. Detailed Construction and Operation of Shaft Assembly 100

The construction of shaft assembly 100 is best seen in FIGS. 16–20. The principal structural member of shaft assembly 100 is tubular member 160 which is fixedly connected adjacent its proximal end to the frame structure 32 of actuator assembly 20. Cables 106 and 108 pass freely through tube 160. The proximal portion of tubular stem member 142 fits into the distal end of tube 160 and is rotatable relative to tube 160 to provide articulation 40. Cables 106 and 108 also pass freely through stem 142 into fastener holding part 210 which is pivotaly mounted on the distal end of stem 142 to provide articulation 110.

Stem 142 is retained in tube 160 by the projection of inwardly extending tube shoulders 162 into annular stem groove 144. Another inwardly extending tube shoulder 164 extends into stem groove 146. Groove 146 is interrupted on one side by stop member 148. Accordingly, stem 142 can rotate in either direction relative to tube 160 until stop member 148 contacts shoulder 164. Elements 148 and 164 therefore cooperate to provide stop means for articulation 140.

Tube 160 is surrounded by another tubular structure including tube 170, collar 180, bushings 184 and 186, thrust ring 188, and locking ring 90. Tube 170 and locking ring 190 are rotatable relative to tube 160. Collar 180 is prevented from rotating relative to tube 160 by projection of collar keys 181 into tube keyways 166. Bushings 184 and 186 are made of a compressible material such as rubber. Thrust ring 188 is made of a relatively low friction material such as polytetrafuoroethyene to facilitate rotation of locking ring 190 relative to elements 180, 184, and 186. Tube 170 is constrained to rotate with stem 142 by virtue of the projection of stem keys 150 into keyways 172 near the distal end of tube 170. Arcuate toothed rack 174 adjacent the distal end of tube 170 engages toothed pinion segment 116 on faslener hoding part 210. Elements 116 and 170 are concentric with axis 112. Proximal-facing teeth 176 on the proximal end of tube 170 engage distal-facing teeth 182 on collar 180. The end surfaces 178a and 178b of rack 174 respectively cooperate with the two side plates 218 of fastener holding part 210 to stop the pivoting of fastener applying assembly 200 about axis 112 when assemby 200 has been pivoted about 90° to either side of axis 102. Accordingly, surfaces 178 and plates 218 cooperate to provide stop means for articulation 110.

In the unlocked position, locking ring 190 is rotated so that proximally extending teeth 192 extend into relatively deep notches 40a in the distal end of main body 30. In this position of locking ring 190, bushings 184 and 186 are only very liqhtly compressed between thrust ring 188 and collar 180. Accordingly, collar 80 and tube 170 are relatively lightly and resiliently urged in the distal direction. Teeth 182 and 176 are the:efo:e only lightly held in engagement with one another, and that engagement can be relatively easily overcome when fastener applying assembly 200 is deliberatey rotated relative to actuator assembly 20 about axis 102. However, the engagement of teeth 182 and 176 is sufficient to releasably hold articulation 140 in any rotational position in which teeth 182 and 176 are engaged. Teeth 182 and 176 and their associated elements therefore comprise detent means for releasably retaining articulation 140 in any of a plurality of rotational positions. On the other hand, when locking ring 190 is rotated so that teeth 192 are displaced from notches 40a (e.g., to relatively shallow notches 40b), locking ring 190 is thereby shifted somewhat in the distal direction. As a result, bushings 84 and 186 are more highly compressed, and collar 180 and tube 170 are strongly urged in the distal direction. This causes teeth 182 and 176 to engage one another much more securely, thereby locking articulation 140 in its current rotational position.

The above-described structure operates in a similar manner in relation to rack 174 and pinion 116. When locking ring teeth 92 are aligned with notches 40a, rack 174 engages pinion 116 only relatively lightly, and elements 116 and 174 therefore act as detent means for releasably holding articulation 110 in any of a plurality of rotational positions. When locking ring teeth 92 are not aligned with notches 40a, rack 174 engages pinion 116 much more securely, thereby locking articulation 110 in its current position.

In use, the surgeon typically manually rotates fastener applying assembly 200 relative to actuator assembly 20 about either or both of articulation axes 102 and 112. Detent elements 116, 174, 176, and 182 releasably hold assemblies 20 and 200 in the selected relative positions. When the surgeon is satisfied with the relative positions of assemblies 20 and 200, the surgeon rotates locking ring 190 so that teeth 192 move from notches 40a to notches 40b thereby locking articulations 110 and 140 in their current positions. If further adjustment is required, locking ring 190 can be rotated again to align teeth 192 with notches 40a, thereby unlocking articulations 110 and 140.

IV. Detailed Construction and Operation of Fastener Applying Assembly 200

Considering now the detailed construction and operation of fastener applying assembly 200 as shown in FIGS. 6–15, fastener holding part 210 is, as has been mentioned, pivotally mounted on the distal end of stem 142 to provide articulation 110. Movably mounted on each side of fastener holding part 210 is a frame mounting cam plate 260a or 260b. Each of cam plates 260 is sandwiched between fastener holding part 210 and the adjacent lateral side of the proximal leg 282 of frame structure 280. Cam plates 260 are guided for vertical reciprocation relative to fastener holding part 210 by projection of cam followers 262 into cam slots 216 in the sides of fastener holding part 210. Frame 280 is positioned in relation to fastener holding part 210 by the projection of cam followers 286 into cam slots 264 in cam plates 260, by the projection of finger 288 between fastener holding part side plates 218, and by the projection of pin 289 into slots 220 in plates 218. Frame 280 is resiliently urged in the distal direction by prestressed compression coil spring 224 acting between fastener holding part 210 and frame 280.

Each of cam plates 260 has a finger 266 which extends into a vertical opening 222 near the rear of fastener holding part 20. Fingers 266 overlap one another inside opening 222, and the distal end of clamp actuator cable 106 is anchored to the fingers where they overlap (see FIG. 7). Cam plates 260 are resiliently urged upward relative to fasener holding part 210 by prestressed compression coil spring 226 acting between fingers 266 and a surface of fastener holding part 210.

In order to reach fingers 266, the distal end portion of cable 106 is redirected approximately 90° by the distal end portion of stem 142 from an alignment in shaft assembly 100 parallel to axis 102 to an alignment in fastener holding part 210 parallel to axis 112 (see FIGS. 7 and 9–13). Accordingly, when clamp actuator 50 pulls cable 106 in the proximal direction, the distal end of cable 106 pulls cam plates 260 vertically down relative to fastener holding part 210 as shown progressively in FIGS. 9–12. The presence of pin 289 in slots 220 prevents frame 280 from moving downwardly with cam plates 260. Accordingly, cam followers 286 are constrained to move up along cam slots 264, thereby causing frame 280 to move in the proximal direction. Pin 289 moves with frame 280 in the proximal direction, traversing slots 220. Cam slots 264 are shaped to cause distal frame leg 284 to first pivot into parallelism with the distal face of fastener holding part 210, and to then translate proximally toward fastener holding part 210 so that at the end of the stroke of clamp actuator 50, the tissue 12 to be fastened is clamped between the distal face of fastener holding part 210 and the parallel proximal face of anvil part 290.

Figure 9:
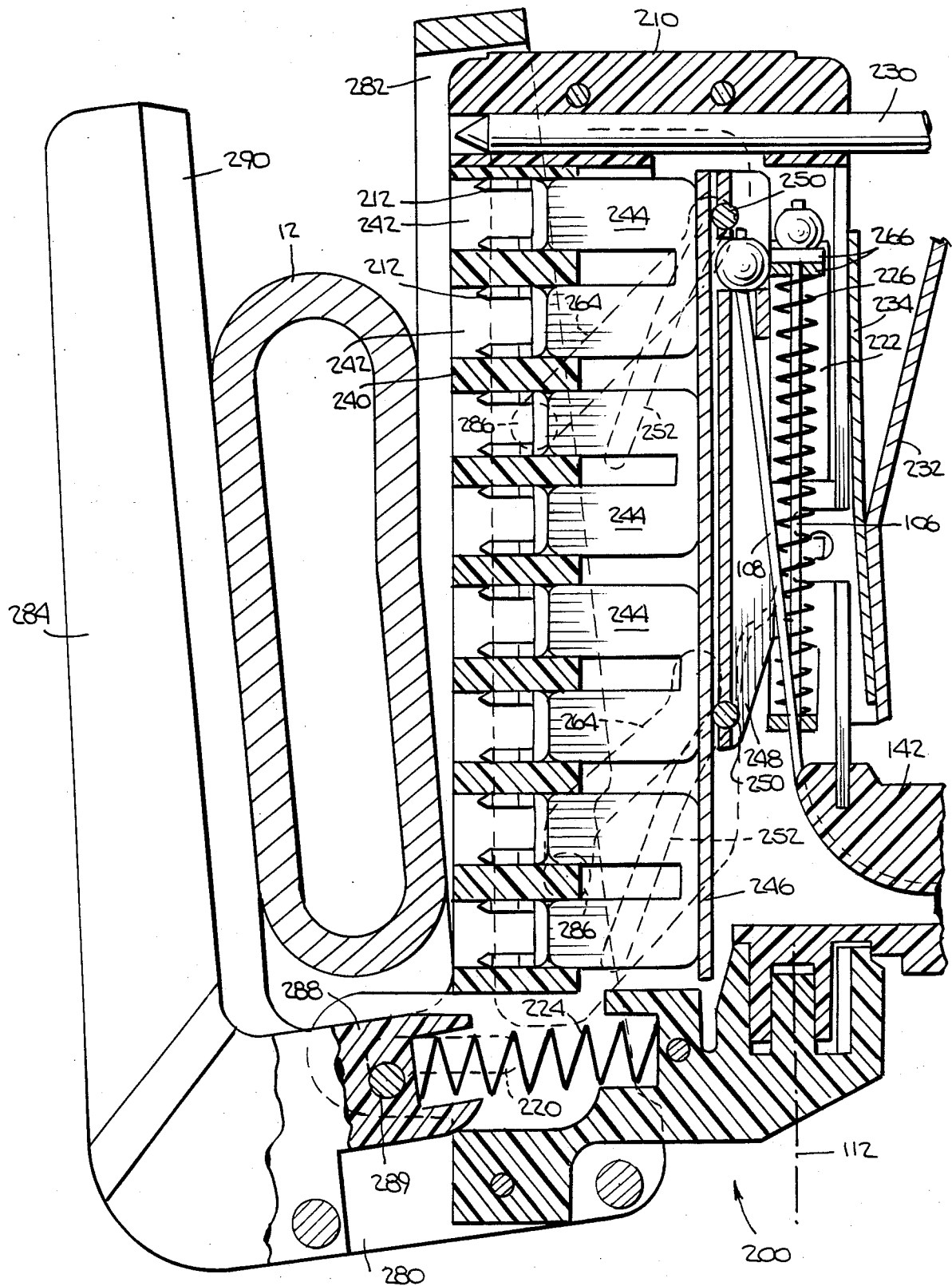
FIG. 9 is a partly sectional elevational view of the distal portion of the apparatus of FIG. 1 in the condition shown in FIG. 2.
Figure 10:
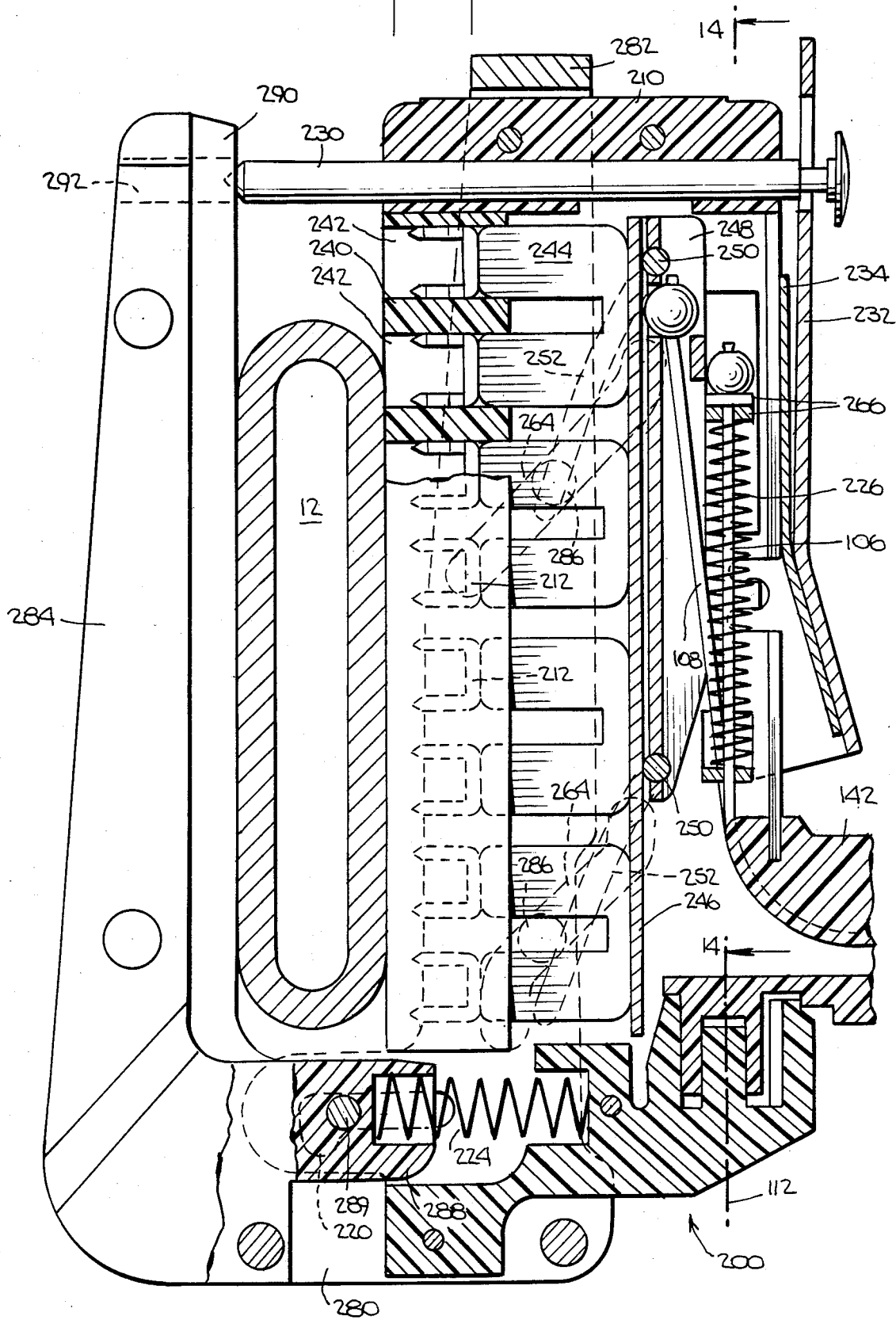
FIGS. 10-13 are views similar to FIG. 9 showing successive stages in the operating cycle of the apparatus of FIG. 1.
Figure 11:
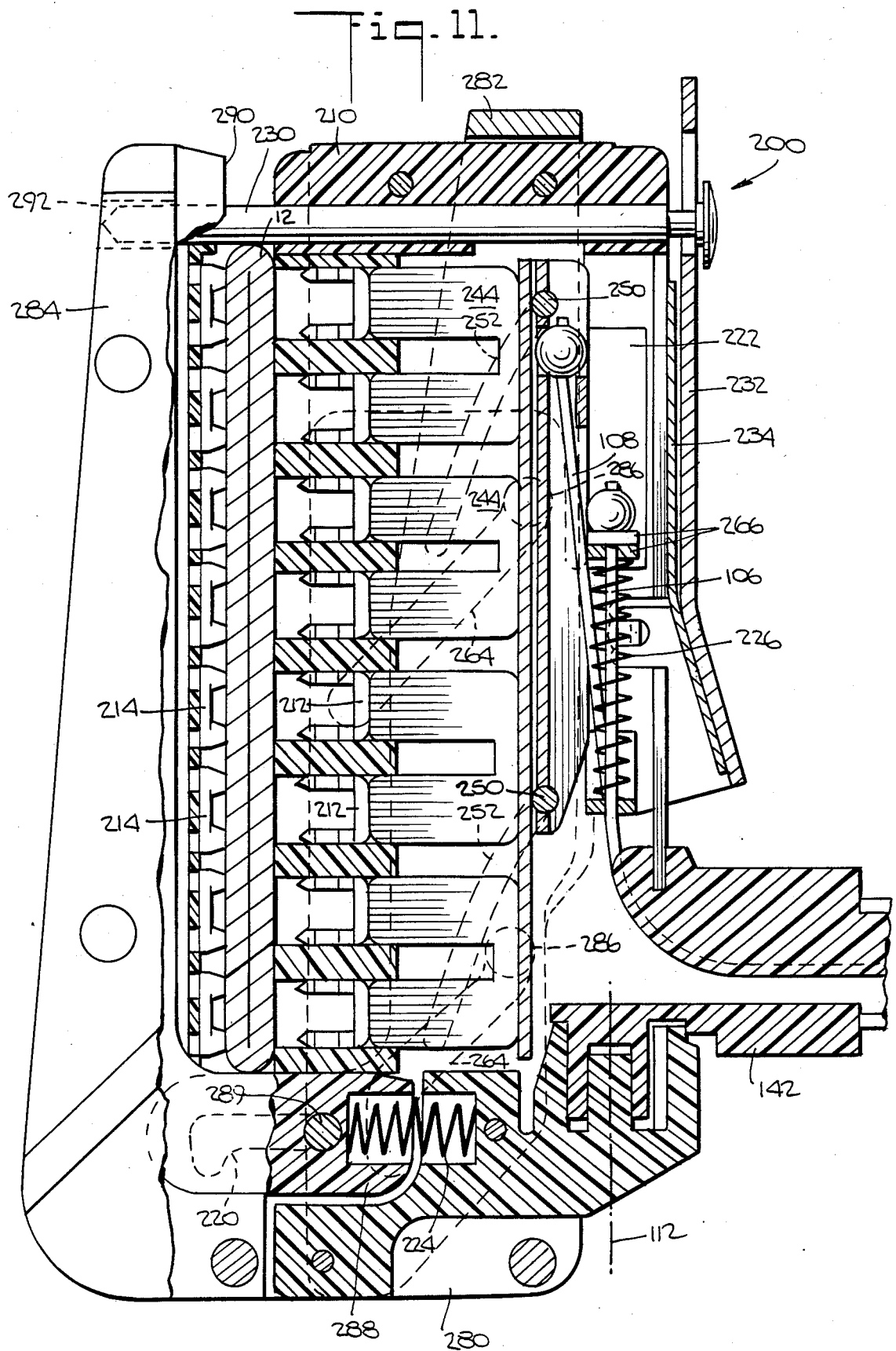
Figure 12:
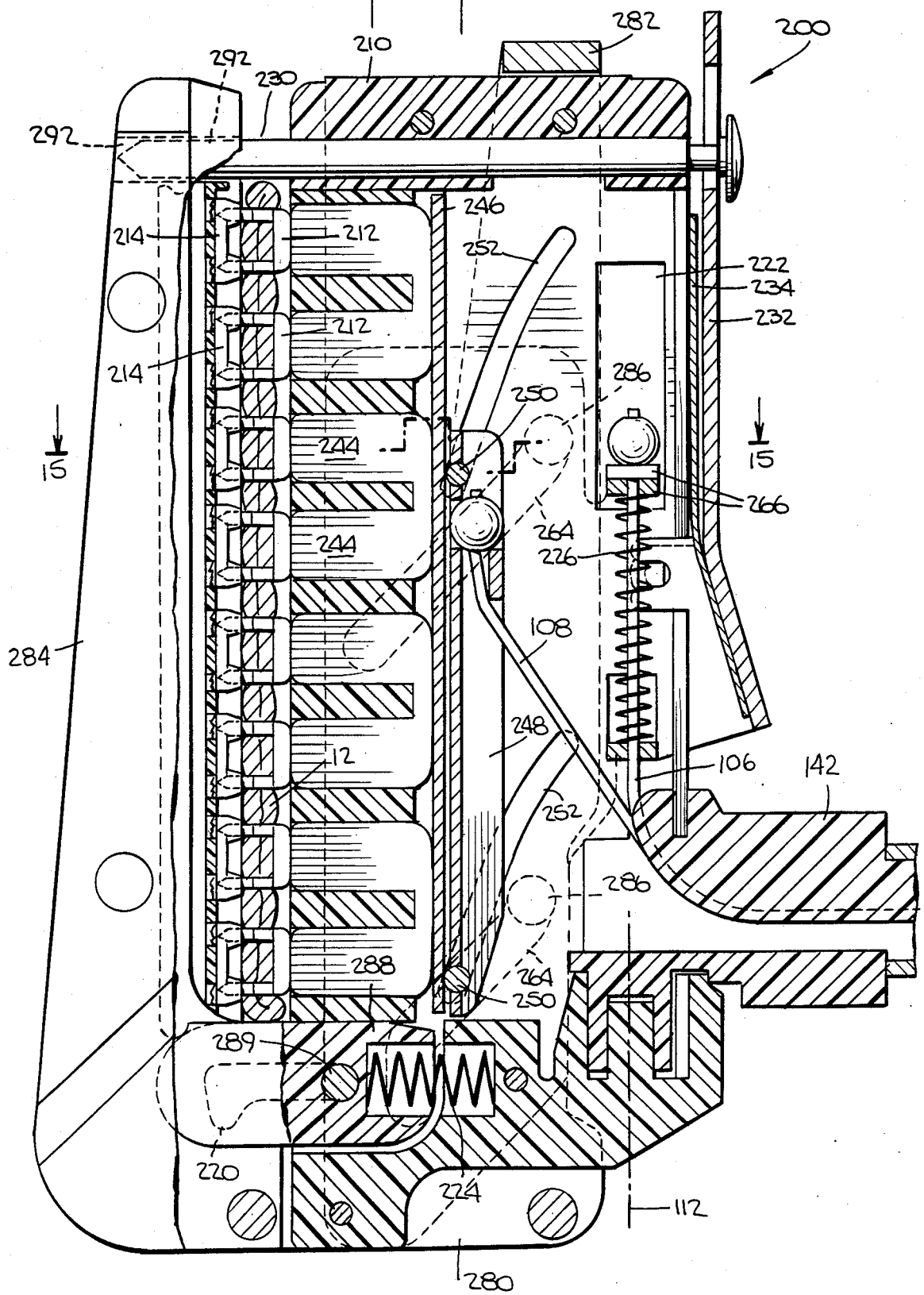

Proper alignment between fastener holding part 210 and anvil part 290 is facilitated by alignment pin 230 which automatically extends from fastener holding part 20 into anvil part 290 as tissue 12 is clamped. Alignment pin 230 is reciprocated by pin carrier 232 which is pivotally mounted on the rear of fastener holding part 210. Pin carrier 232 is resiliently biased to retract pin 230 in the proximal direction as shown in FIG. 9 by leaf spring 234. The lower portion of pin carrier 232 includes cam follower surfaces 236 which are in contact with cam surfaces 268 on the proximal edges of cam plates 260. Surfaces 236 and 268 are cooperatively shaped to allow spring 234 to proximally retract alignment pin 230 when cam plates 260 are in their uppermost positions, and to pivot pin carrier 232 and thereby distally extend alignment pin 230 as cam plates 260 are pulled down by cable 106. By the time clamp actuator 50 has reached the intermediate rest position shown in FIG. 3 (with tooth 59 engaging step 38), alignment pin 230 is fully extended and has begun to enter anvil aperture 292 as shown in FIG. 10. Accordingly, alignment pin 230 helps to confine tissue 12 to the space between fastener holding part 210 and anvil part 290 during any instrument placement adjustments the surgeon may wish to make and during final clamping of the tissue. When tissue clamping continues as shown in FIG. 11, anvil aperture 292 is pulled farther onto the distal end of alignment pin 230, thereby ensuring proper alignment of fastener holding part 210 and anvil part 290.

After tissue 12 has been clamped as described above, fastener parts 212 are driven by elements best seen in FIGS. 7–13 and 15. Fastener parts 212 are initially disposed in apertures 242 in holder 240 which forms the distal portion of fastener holding part 210. A pusher finger 244 extends into the rear of each aperture 242. Pusher fingers 244 may be advantageously interconnected in small groups (e.g., pairs) to reduce the number of separate parts and to stabilize the individual pusher fingers without creating a single large pusher structure that might tend to bind in apertures 242. The proximal ends of all of pusher fingers 244 are spanned by a single rigid pusher follower member 246. Pusher actuator 248 is located on the proximal side of follower 246 and is supported by cam follower pins 250 which extend into cam slots 252 in the side plates 218 of fastener holding part 210.

The distal end of fastener actuator cable 108 is attached to pusher actuator 248. As in the case of cable 106, the distal end portion of cable 108 is redirected approximately 90° by the distal end portion of stem 142 from an alignment in shaft assembly 100 parallel to axis 102 to an alignment in fastener holding part 210 parallel to axis 112 in order to reach pusher actuator 248. When fastener actuator 70 is operated to pull cable 108 in the proximal direction, the distal end of cable 108 pulls down on pusher actuator 248. As pusher actuator 248 moves down, it is also forced to move in the distal direction by cooperation of elements 250 and 252 (see FIG. 12). The distal motion of pusher actuator 248 is imparted to pusher fingers 244 via pusher follower 246, thereby driving fastener parts 212 partly through tissue 12 and into interlocking engagement with retainer parts 214 to fasten the tissue.

Figure 13:
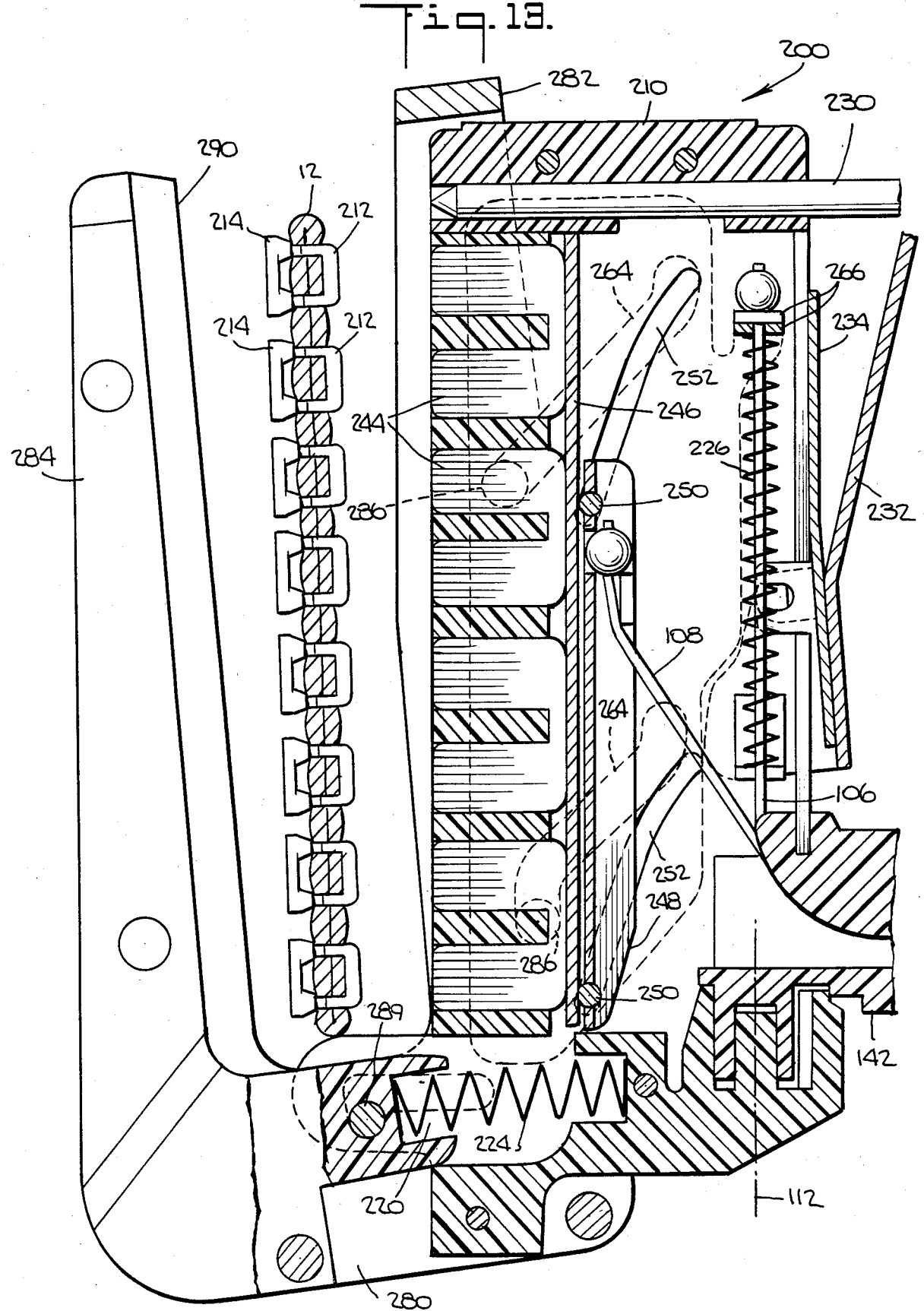
Figure 16:
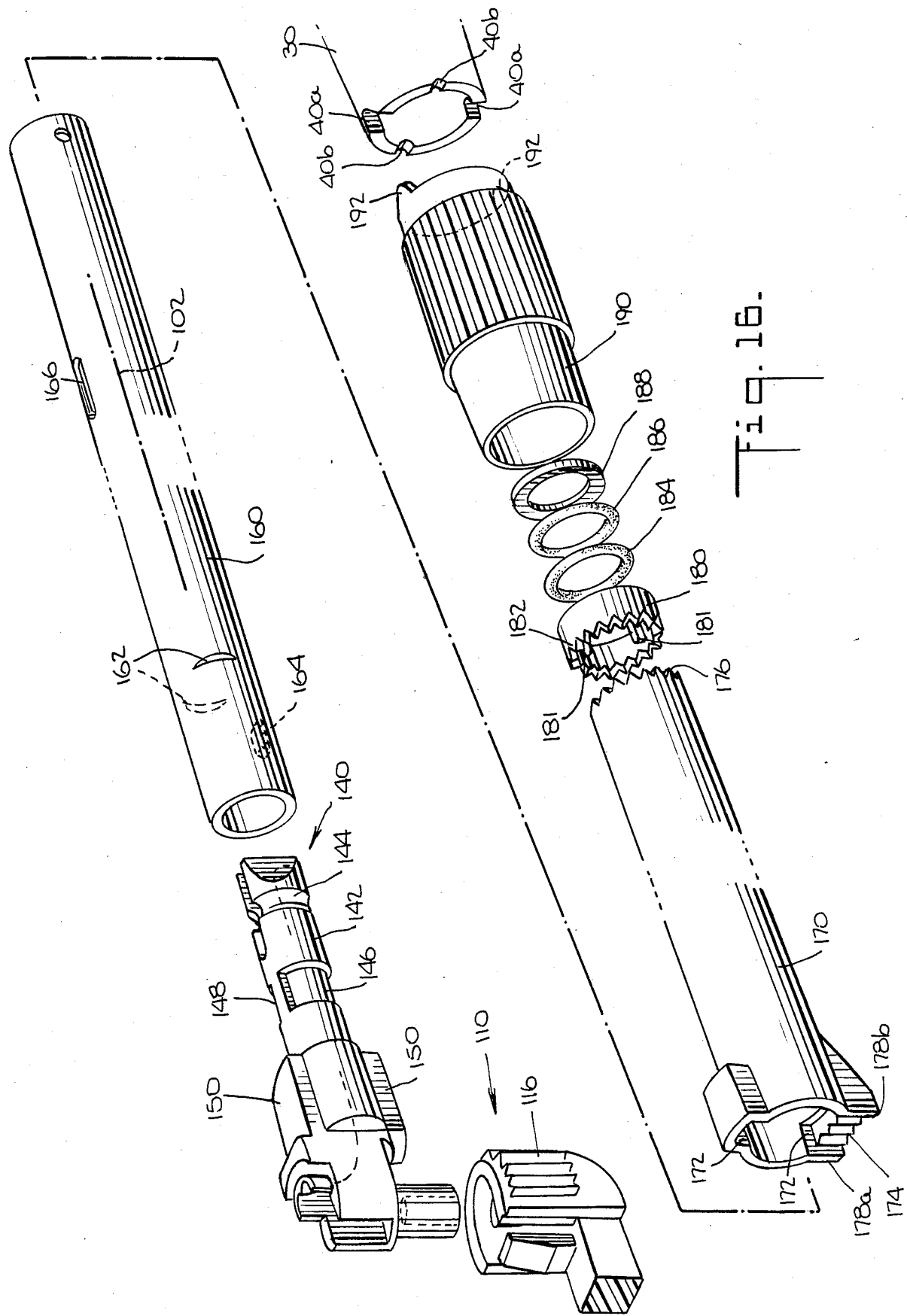
FIG. 16 is an exploded perspective view of the intermediate portion of the apparatus of FIG. 1.
Figure 17:
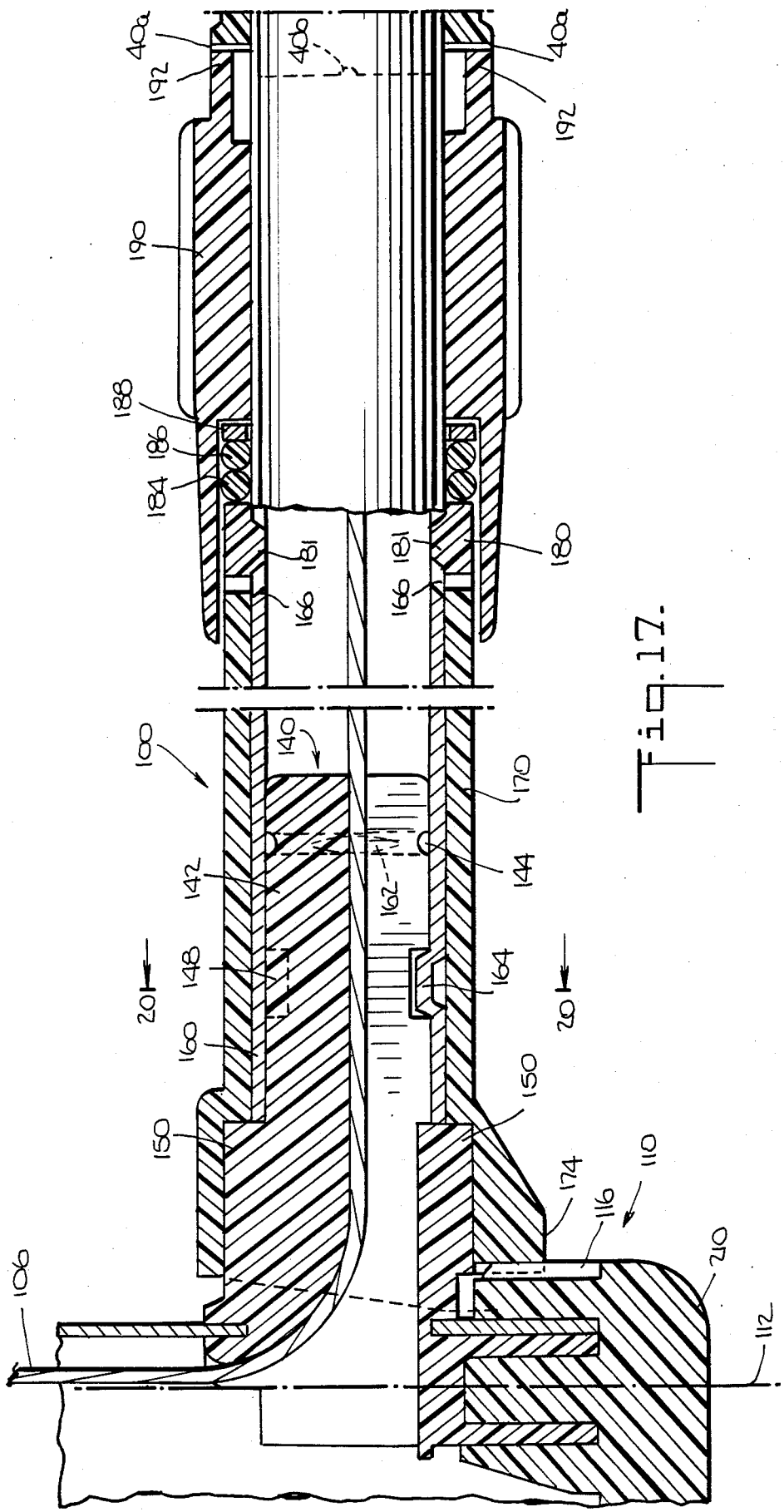
FIG. 17 is a partly sectional elevational view of the intermediate portion of the apparatus of FIG. 1.
Figure 18:
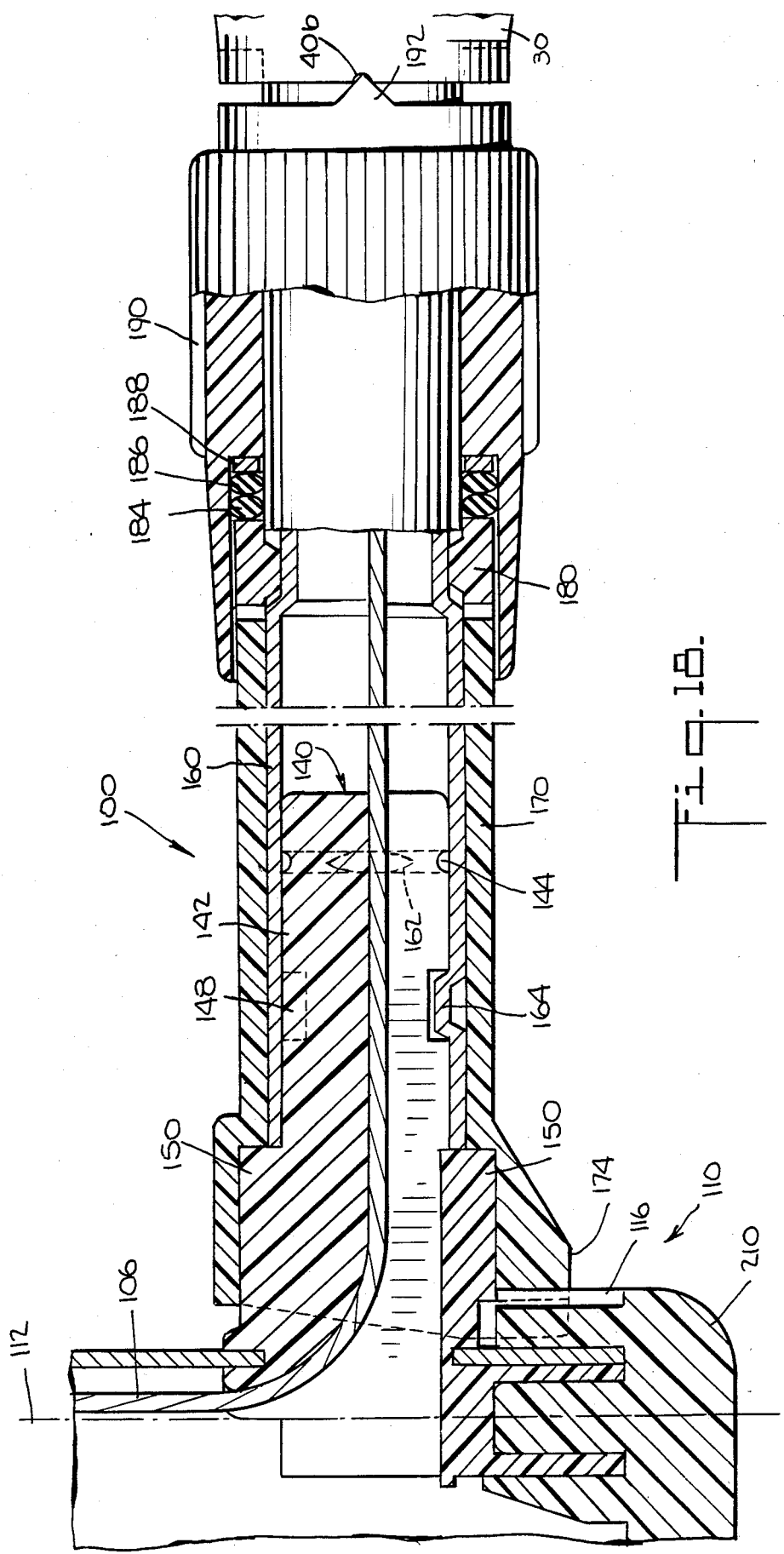
FIG. 18 is a view similar to FIG. 17 showing a different operating condition of the apparatus of FIG. 1.
Figure 19:
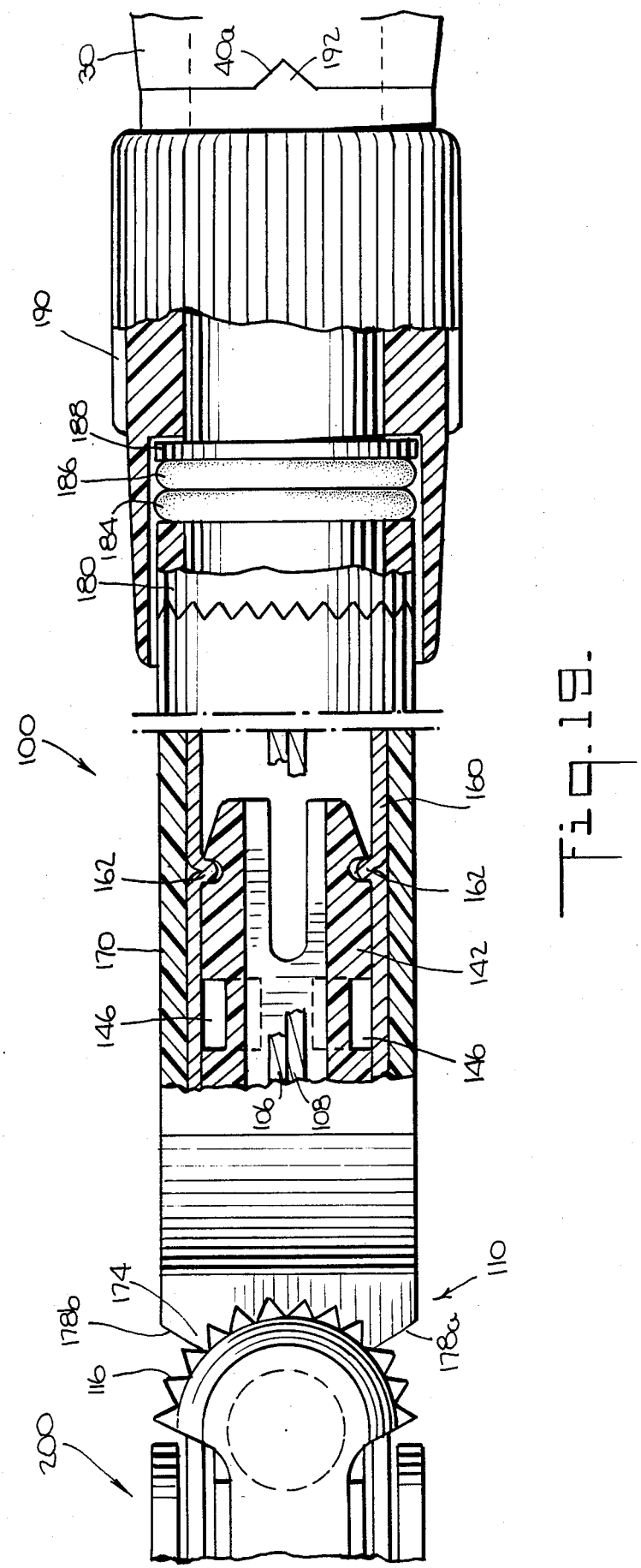
FIG. 19 is a partly sectional bottom plan view of the intermediate portion of the apparatus of FIG. 1 in the condition shown in FIG. 17.
Figure 20:
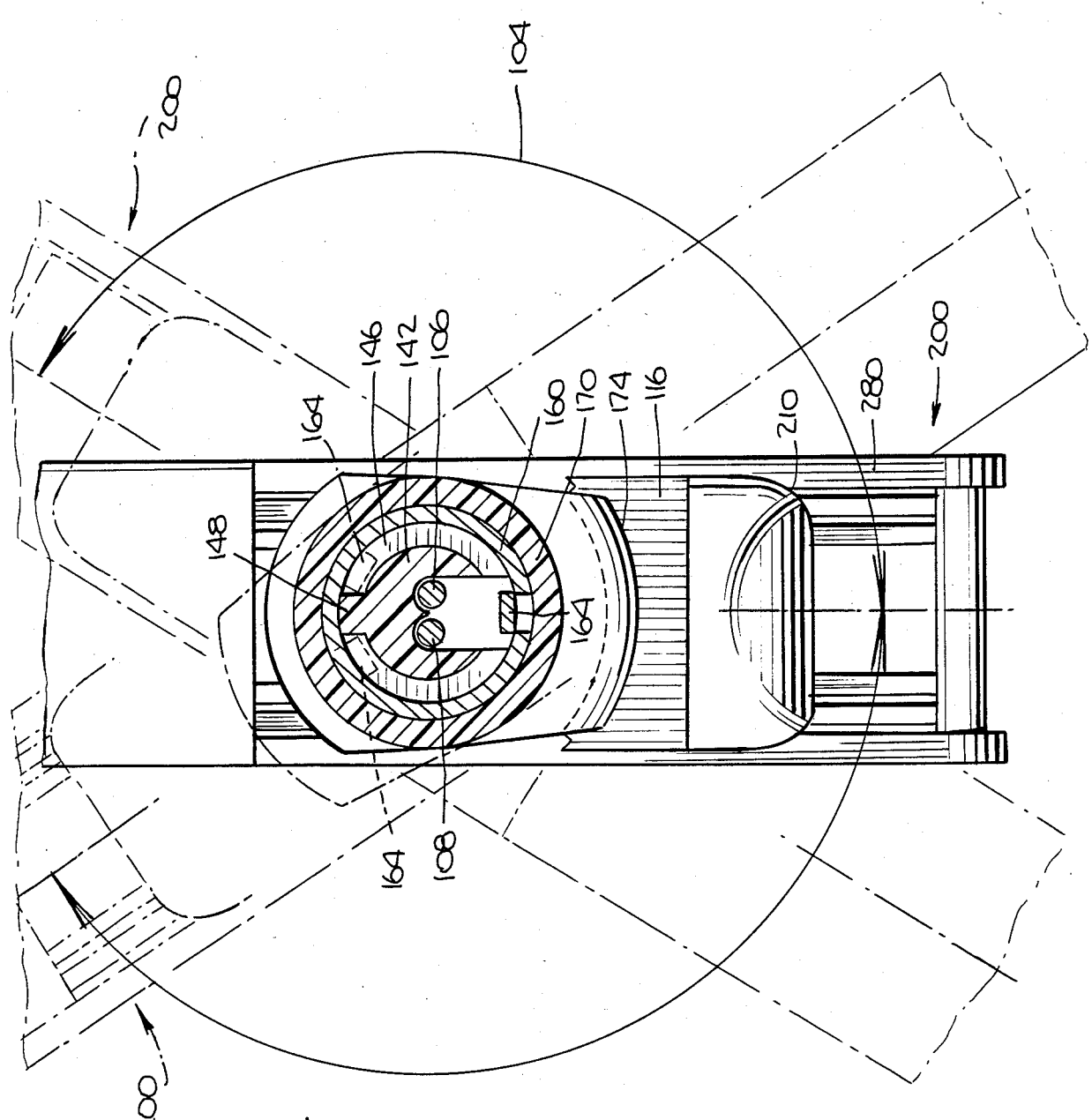
FIG. 20 is a sectional view taken along the line 20—20 FIG. 17.
Figure 21:
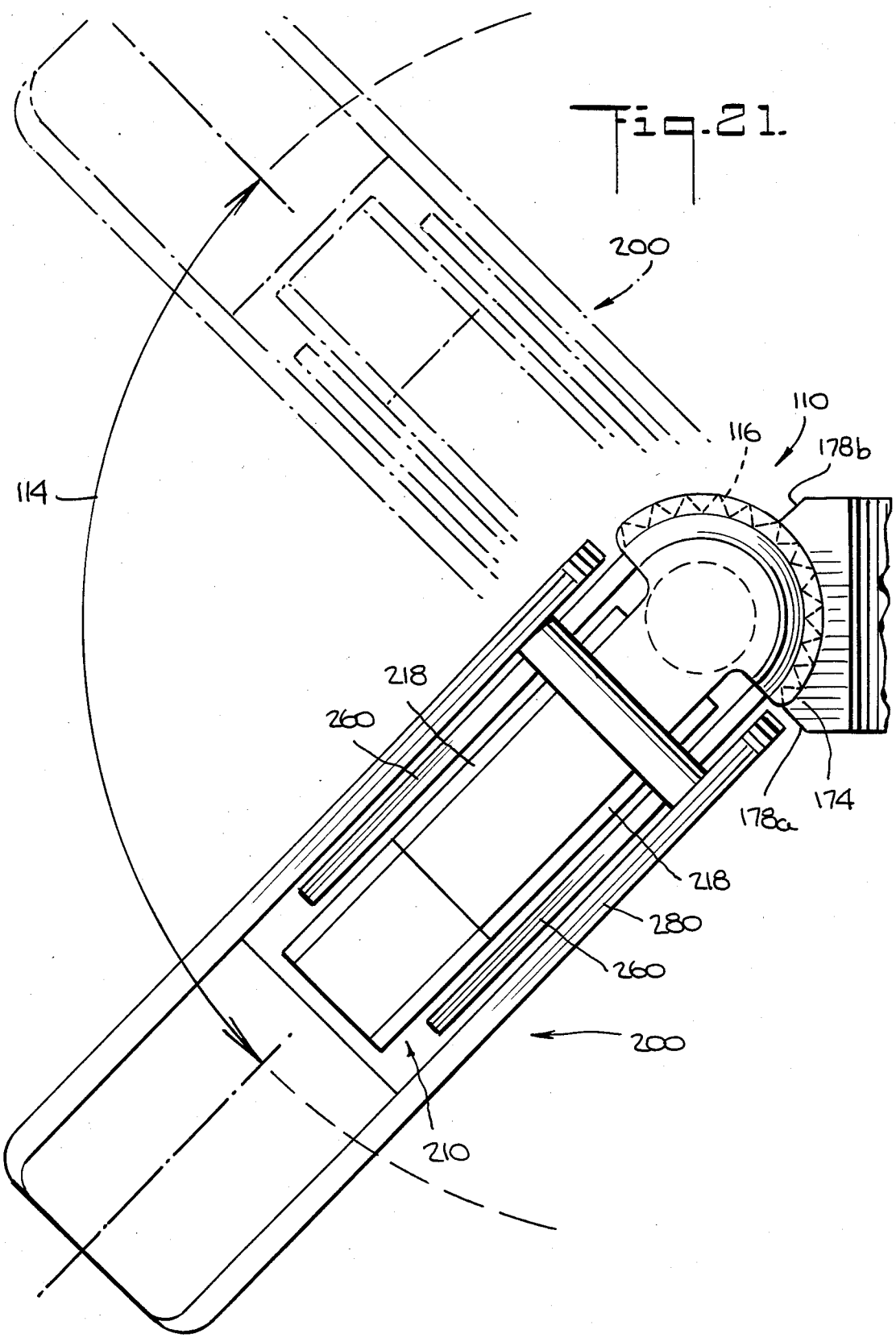
FIG. 21 is a bottom plan view of the distal portion of the apparatus of FIG. 1.

After tissue 12 has been fastened as described above, the clamping pressure on the tissue is released by raising clamp actuator 50. Springs 224 and 226 restore cam plates 260 and frame 280 to their initial positions, and spring 234 causes proximal retraction of alignment pin 230. Accordingly, fastened tissue 12 is released from the instrument as shown in FIG. 13 and the instrument can be removed from the surgical site.

It should be noted that the work required for tissue clamping and fastener application is transmitted from actuator assembly 20 to fastener applying assembly 200 by proximally movable tension force transmitting members 106 and 108 which are both transversely and torsionally flexible. The transverse flexibility of cables 106 and 108 allows them to be redirected adjacent the distal end of stem 142. It should also be noted that the path lengths of cables 106 and 108 are substantially unaffected by the rotational positions of articulations 110 and 140 because each cable is substantially coincident with the axis 102 or 112 of each articulation at the location of that articulation. For example, cables 106 and 108 are both substantially coincident with axis 102 at the point where stem 142 rotates relative to tube 160. Accordingly, cables 106 and 108 twist slightly when articulation 140 is operated, but the path lengths of cables 106 and 108 do not change significantly. Similarly, cables 106 and 108 are both substantially coincident with axis 112 at the point where fastener holding part 210 is rotatably mounted on stem 142. Thus again, operation of articulation 140 causes cables 106 and 108 to twist slightly but does not significantly alter the path length of either cable. (As used in this context, the term "coincident" means that cables 106 and 108 either approximately intersect or are approximately coaxial with the specified axis at the specified location.) The transverse and torsional flexibility of cables 106 and 108 and the constant path lengths of those cables facilitate articulation of the instrument as described above and allow operation of the instrument with articulations 110 and 140 at any of their rotational positions.

We claim:

1. Surgical fastener applying apparatus comprising:
    a distal fastener applying assembly including a fastener holding part initially containing at least one surgical fastener, (b) an anvil part movable relative to the fastener holding part for clamping tissue to be fastened between the fastener holding part and the anvil part, and (c) first means for driving the fastener from the fastener holding part at least partially through the clamped tissue to the anivil part;
    a proximal actuator assembly including second means for producing the work necessary to operate the first means; and
    a longitudinal shaft assembly for supporting the fastener applying assembly relative to the actuator assembly and for transmitting the work produced by the second means to the first means, the shaft assembly including a first articulation for allowing rotation of the fastener applying assembly relative to the actuator assembly about a first axis which is transverse to the longitudinal axis of the shaft assembly, the shaft assembly being operative to transmit work from the second means to the first means at any rotational position of the first articulation, and the shaft assembly being substantially inflexible about all other axes parallel to the first axis, the shaft assembly further including first stop means for preventing the fastener applying assembly from rotating relative to the acutator assembly for more than a predetermined amount in either direction about the first axis.

2. The apparatus defined in claim 1 where in the first stop means allows the fastener applying assembly to rotate at least 180° about the first axis relative to the actuator assembly.

3. Surgical fastener applying apparatus comprising:
    a distal fastener applying assembly including (a) a fastener holding part initially containing at least one surgical fastener, (b) an anvil part movable relative to the fastener holding part for clamping tissue to be fastened between the fastener holding part and the anvil part, and (c) first means for driving the fastener from the fastener holding part at least partially through the clamped tissue to the anvil part;
    a proximal actuator assembly including second means for producing the work necessary to operate the first means; and
    a longitudinal shaft assembly for supporting the fastener applying assembly relative to the actuator assembly and for transmitting the work produced by the second means to the first means, the shaft assembly including a first articulation for allowing rotation of the fastener applying assembly relative to the actuator asssembly about a first axis which is transverse to the longitudinal axis of the shaft assembly, the shaft assembly being operative to transmit work from the second means to the first means at any rotational position of the first articulation, and the shaft assembly being substantially inflexible about all other axes parallel to the first axis, the shaft assembly further including a second articulation for allowing rotation of the fastener applying assembly relative to the actuator assembly about the longtitudianl axis of the shaft assembly, the shaft assembly being operative to transmit work from the second means to the first means at any rotational position of the second articulation, the shaft assembly also including second detent means for releasably retaining the second articulation in any of a plurality of rotational positions.

4. Surgical fastener applying apparatus comprising:
    a distal fastener applying assembly including (a) a fastener holding part initially containing at least one surgical fastener, (b) an anvil part movable relative to the fastener holding part for clamping tissue to be fastened between the fastener holding part and the anvil part, and (c) first means for driving the fastener from the fastener holding part at least partially through the clamped tissue to the anvil part;

a proximal actuator assembly including second means for producing the work necessary to operate the first means; and a longitudinal shaft assembly for supporting the fastener applying assembly relative to the actuator assembly and for transmitting the work produced by the second means to the first means, the shaft assembly including a first articulation for allowing rotation of the fastener applying assembly relative to the actuator assembly about a first axis which is transverse to the longitudinal axis of the shaft assembly, the shaft assembly being operative to transmit work from the second means to the first means at any rotational position of the first articulation, and the shaft assembly being substantially inflexible about all other axes parallel to the first axis, the shaft assembly further including a second articulation for allowing rotation of the fastener applying assembly relative to the actuator assembly about the longitudinal axis of the shaft assembly, the shaft assembly being operative to transmit work from the second means to the first means at any rotational position of the second articulation, the shaft assembly also including second locking means for locking the second articulation in any of a plurality of rotational positions.

5. Surgical fastener applying apparatus comprising:

a distal fastener applying assembly including (a) a fastener holding part initially containing at least one surgical fastener, (b) an anvil part movable relative to the fastener holding part for clamping tissue to be fastened between the fastener holding part and the anvil part, and (c) first means for driving the fastener from the fastener holding part at least partially through the clamped tissue to the anvil part;

a proximal actuator assembly including second means for producing the work necessary to operate the first means; and a longitudinal shaft assembly for supporting the fastener applying assembly relative to the actuator assembly and for transmitting the work produced by the second means to the first means, the shaft assembly comprising a tube and means including a single first articulation at one end of said tube for allowing rotation of the fastener applying assembly relative to the actuator assembly about a first axis which is transverse to the longitudinal axis of the shaft assembly, the shaft assembly further including a second articulation for allowing rotation of the fastener applying assembly and the first axis relative to the actuator assembly about the longitudinal axis of the axis of the shaft assembly, the shaft assembly being operative to transmit work from the second means to the first means at any rotational position of the first articulation and at any rotational positional of the second articulation, and the shaft assembly being substantially inflexible about all axes other than the first axis transverse to the longitudinal axis of the shaft assembly.

6. Surgical fastener applying apparatus comprising:

a distal fastener applying assembly including (a) a fastener holding part initially containing at least one surgical fastener, (b) an anvil part movable relative to the fastener holding part for clamping tissue to be fastened between the fastener holding part and the anvil part, and (c) first means for driving the fastener from the fastener holding part at least partially through the clamped tissue to the anvil part;

a proximal actuator assembly including second means for producing the work necessary to operate the first means; and a longitudinal shaft assembly for supporting the fastener applying assembly relative to the actuator assembly and for transmitting the work produced by the second means to the first means, the shaft assembly including a first articulation for allowing rotation of the fastener applying assembly relative to the actuator assembly about a first axis which is transverse to the longitudinal axis of the shaft assembly, the shaft assembly being operative to transmit work from the second means to the first means at any rotational position of the first articulation, and the shaft assembly being substantially inflexible about all other axes parallel to the first axis, the shaft assembly further including first detent means for releasably retaining the first articulation in any of a plurality of rotational positions so that the fastener applying assembly can be rotated from one rotational position to another merely by a manual application of a torque above a predetermined threshold.

7. The apparatus defined in claim 1 wherein the first axis is perpendicular to the longitudinal axis of the shaft assembly.

8. The apparatus defined in claim 7, wherein the first axis is adjacent to the distal end of the shaft assembly.

9. The apparatus defined in claim 6 wherein the shaft assembly further includes first locking means for locking the first articulation in any of a plurality of rotational positions so that a rotation of said fastener applying assembly from one rotational position to another upon an actuation of said locking means requires a deactuation of said locking means in addition and prior to a manual application of a torque above said predetermined threshold.

10. The apparatus defined in claim 1 wherein the shaft assembly further includes first stop means for preventing the fastener applying assembly from rotating relative to the actuator assembly more than a predetermined amount in either direction about the first axis.

11. The apparatus defined in claim 1 wherein the first stop means allows the fastener applying assembly to rotate at least about 180° about the first axis relative to the actuator assembly.

12. The apparatus defined in claim 6 wherein the shaft assembly further includes a second articulation for allowing rotation of the fastener applying assembly relative to the actuator assembly about the longitudinal axis of the shaft assembly, the shaft assembly being operative to transmit work from the second means to the first means at any rotational position of the second articulation.

13. The apparatus defined in claim 12 wherein the shaft assembly further includes second detent means for releasably retaining the second articulation in any of a plurality of rotational positions.

14. The apparatus defined in claim 12 wherein the shaft assembly further includes second locking means for locking the second articulation in any of a plurality of rotational positions.

15. The apparatus defined in claim 12 wherein the shaft assembly further includes second stop means for preventing the fastener applying assembly from rotating relative to the actuator assembly more than a predetermined amount in either direction about the longitudinal axis of the shaft assembly.

16. The apparatus defined in claim 1 wherein the second stop means allows the fastener applying assembly to rotate at least about 180° about the longitudinal axis of the shaft assembly.

17. The apparatus defined in claim 1 wherein the shaft assembly transmits the work produced by the second means to the first means via a first proximally movable tension force transmitting member which is transversely and torsionally flexible adjacent the first articulation.

18. The apparatus defined in claim 17 wherein the first member is coincident with the first axis adjacent the first articulation.

19. The apparatus defined in claim 6 wherein the actuator assembly further includes third means for producing the work necessary to move the anvil part relative to the fastener holding part to clamp the tissue, and wherein the shaft assembly further includes fourth means for operatively transmitting the work produced by the third means to the fastener applying assembly, the fourth means being operative to transmit work from the third means to the fastener applying assembly at any rotational position of the first articulation.

20. The apparatus defined in claim 1 wherein the fourth means comprises a second proximally movable tension force transmitting member which is transversely and torsionally flexible adjacent the first articulation.

21. The apparatus defined in claim 20 wherein the second member is coincident with the first axis adjacent the first articulation.

22. The apparatus defined in claim 6 wherein the fastener applying assembly applies a plurality of surgical fasteners in a linear array whose longitudinal axis is transverse to the longitudinal axis of the shaft assembly, and wherein the first axis is parallel to the longitudinal axis of the linear array.

23. The apparatus defined in claim 22 wherein the shaft assembly transmits the work produced by the second means to the first means via a first proximally movable member, wherein the first means drives the fasteners in the distal direction, and wherein the fastener applying assembly further includes means for converting the proximal motion of the first member to distal motion of the first means.

* * * * *